(12) United States Patent
Wright et al.

(10) Patent No.: US 10,016,383 B2
(45) Date of Patent: Jul. 10, 2018

(54) INHIBITORS OF METALLO-β-LACTAMASE-ENZYMES

(71) Applicant: McMaster University, Hamilton (CA)

(72) Inventors: Gerry Wright, Cambridge (CA); Wenliang Wang, Toronto (CA); Andrew King, Waterdown (CA)

(73) Assignee: McMaster University, Hamilton (CA)

( * ) Notice: Subject to any disclaimer, the term of this patent is extended or adjusted under 35 U.S.C. 154(b) by 0 days.

(21) Appl. No.: 14/888,764

(22) PCT Filed: May 7, 2014

(86) PCT No.: PCT/CA2014/050434
§ 371 (c)(1),
(2) Date: Nov. 3, 2015

(87) PCT Pub. No.: WO2014/179885
PCT Pub. Date: Nov. 13, 2014

(65) Prior Publication Data
US 2016/0081960 A1 Mar. 24, 2016

Related U.S. Application Data

(60) Provisional application No. 61/820,277, filed on May 7, 2013.

(51) Int. Cl.
| | | |
|---|---|---|
| *A61K 31/198* | (2006.01) | |
| *A61K 31/407* | (2006.01) | |
| *A61K 31/4196* | (2006.01) | |
| *A61K 45/06* | (2006.01) | |

(52) U.S. Cl.
CPC .......... *A61K 31/198* (2013.01); *A61K 31/407* (2013.01); *A61K 31/4196* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 6,548,492 B1 | 4/2003 | Al-Dehneh et al. | |
| 2002/0061281 A1 | 5/2002 | Osbakken et al. | |
| 2005/0065141 A1* | 3/2005 | Odink .................. | A61K 31/407 514/210.09 |
| 2006/0233878 A1* | 10/2006 | Bhamare .............. | A61K 9/2018 424/468 |

FOREIGN PATENT DOCUMENTS

| | | | |
|---|---|---|---|
| JP | 60-56941 A | | 2/1985 |
| JP | 62-149616 A | * | 7/1987 |
| JP | 62149616 A | | 7/1987 |
| JP | 06-192081 A | | 7/1994 |
| JP | 2003-514779 A | | 4/2003 |
| JP | 2005-508314 A | | 3/2005 |
| JP | 2008-174478 A | | 7/2008 |
| JP | 2009-273460 A | | 11/2009 |

OTHER PUBLICATIONS

Arai et al. "Aspergillomarasmine A and B, Potent Microbial Inhibitors of Endothelin-Converting Enzyme". Bioscience, Biotechnology and Biochemistry. 1993; 57(11):1944-1945.*
Nunez et al. "The Biosynthetic Gene Cluster for the beta-Lactam Carbapenem Thienamycin in Streptomyces cattleya". Chemistry & Biology. Apr. 2003; 10:301-311.*
Kelly et al. "Mutational Analysis of nocK and nocL in the Nocardicin A Producer Nocardia uniformis". Journal of Bacteriology. Jan. 2005; 187(2):739-746.*
English Machine Translation of JP 62-149616 A. Three pages.*
Palzkill T. "Metallo-Beta-Lactamase Structure and Function". Annals of the New York Academy of Sciences. 2013; 1277:91-104.*
Bush K. "Bench-to-Bedside Review: The Role of Beta-Lactamases in Antiobiotic-Resistant Gram-Negative Infections". Critical Care, 2010; 14:224.*
Willman et al. "Effect of Metallo-Beta-Lactamase Production and Multidrug Resistance on Clinical Outcomes in Patients with Pseudomonas aeruginosa Bloodstream Infection: A Retrospective Cohort Study". BMC Infectious Diseases. 2013; 13:515.*
Aghamiri et al. "Antibiotic Resistance Pattern and Evaluation of Metallo-Beta Lactamase Genes Including bla-IMP and bla-VIM Types in Pseudomonas aeruginosa Isolated from Patients in Tehran Hospitals". ISRN Microbiology. 2014. pp. 1-6.*
Dalhoff et al. "Redefining Penems". Biochemical Pharmacology. 2006; 71:1085-1095.*
STN Registry No. 3262-58-6. "Aspergillomarasmine B". Retrieved from STN Registry File May 24, 2017. One page.*
Daikos et al. "Activity of Imipenem Against VIM-1 Metallo-Beta-Lactamase-Producing Klebsiella pneumoniae in the Murine Thigh Infection Model". Clinical Microbiology and Infection. Feb. 2007; 13(2):202-205. (Year: 2007).*
International Search Report and Written Opinion of corresponding application No. PCT/CA2014/050434 dated Aug. 18, 2014.
Buynak, John D., "β-Lactamase inhibitors: a review of the patent literature (2010-2013)", Expert Opin., Ther. Patents, (2013), vol. 23., No. 11, pp. 1469-1481.
Mikami, Yoji, et al., "Novel Microbial Inhibitors of Angiotensin-converting Enzyme, Aspergillomarasmines A and B", Agric. Biol. Chem., 47, (11), 1983, pp. 2693-2695.
Arai, Koshi, et al., "Aspergillomarasmine A and B, Potent Mictobial Inhibitors of Endothelin-converting Enzyme", Biosci. Biotech. Biochem. 57, (11), 1993, pp. 1944-1945.
King, Andrew et al., "Aspergillomarasmine-A: A potent inhibitor of NDM-s", Presentation, Canadian Society for Microbiology, Jun. 2013.
King, Andrew et al., Aspergillomarasmine A, A Natural Product from Fungi, is a Potent Inhibitor of the VIM and NDM Metallo-β-Lactamases Resorting Carbapenem Activity, Poster, American Society for Microbiology, May 17-20, 2014.

(Continued)

*Primary Examiner* — Leslie A. Royds Draper
(74) *Attorney, Agent, or Firm* — Foley & Lardner LLP

(57) ABSTRACT

The present application relates to combination treatments for bacterial infections. For example, the application relates to the use of one or more β-lactam antibiotics and one or more compounds of Formula I: (I) for treatment of a metallo-B-lactamase-expressing bacterial infection or a disease, disorder or condition arising from a metallo-B-lactamase-expressing bacterial infection.

37 Claims, 3 Drawing Sheets

(56) References Cited

OTHER PUBLICATIONS

Figure 1:
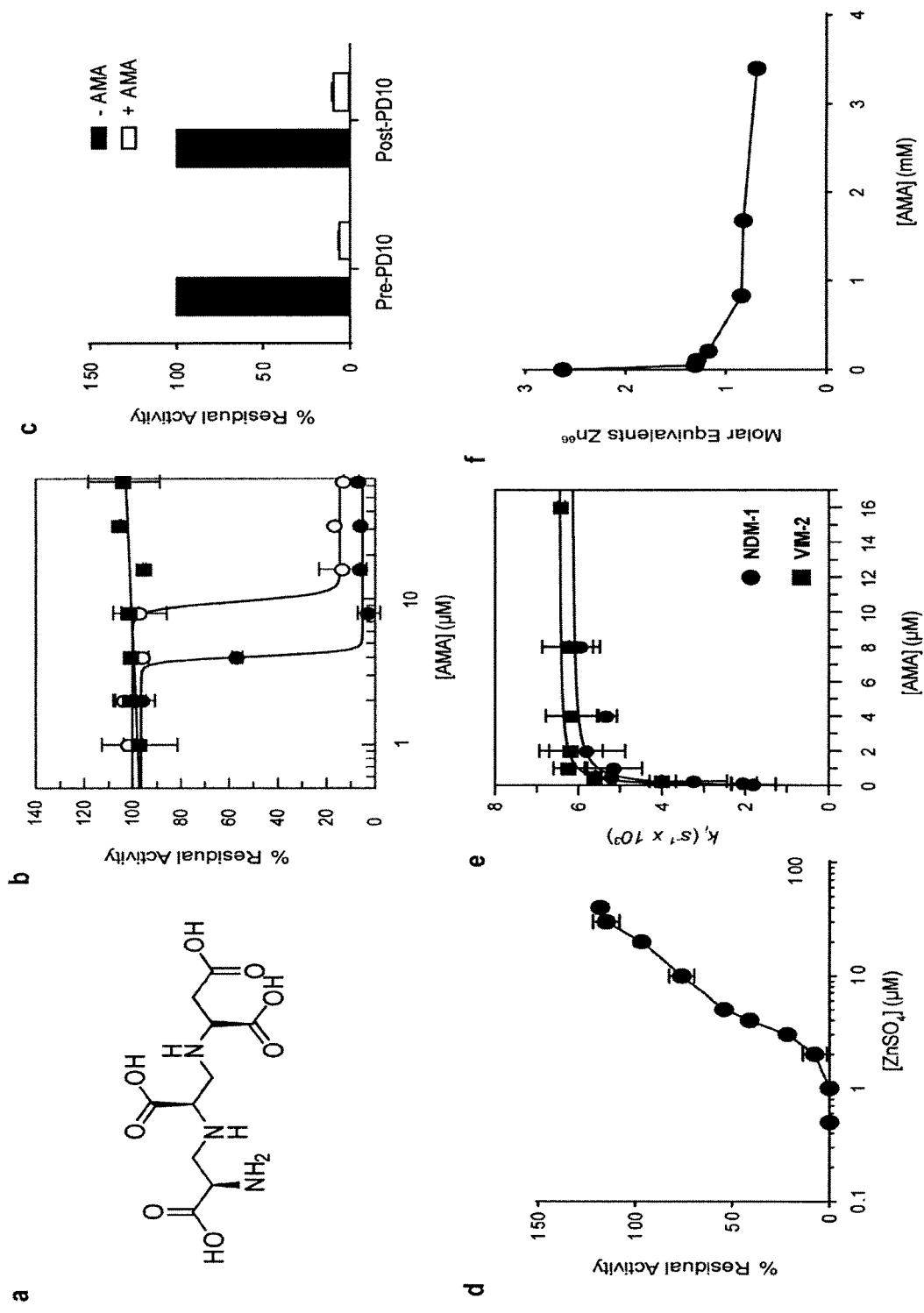

King et al., "New Delhi Metallo-β-Lactamase: Structural Insights into β-Lactam Recognition and Inhibition," Journal of the American Chemical Society, Jun. 19, 2012, 134(28)11362-11365.
Blair et al., "Structure, function and inhibition of RND efflux pumps in Gram-negative bacteria: an update," Curr. Op. Microbiol., 2009, 12:512-519.
Bush, K, "Proliferation and significance of clinically relevant beta-lactamases," Ann. NY Acad. Sci., 2013, 1277:84-90.
Drawz et al., "Three decades of beta-lactamase inhibitors," Clin. Microbiol. Rev., 2010, 23:160-201.
Edelstein et al., "Spread of extensively resistant VIM-2-positive ST235 Pseudomonas aeruginosa in Belarus, Kazakhstan, and Russia: a longitudinal epidemiological and clinical study," Lancet Infect. Dis., 2013, 13:867-876.
Fast et al., "Metallo-beta-lactamase: inhibitors and reporter substrates," Biochim. Biophys. Acta, 2013, 1834:1648-1659.
Frias et al., "New Delhi Metallo-β-Lactamase-Producing *Escherichia coli* Associated with Endoscopic Retrograde Cholangiopancreatography—Illinois, 2013," Morbidity and Mortality Weekly Report, Jan. 3, 2014, 62(51&52):1051.
Gaumann et al.,. "Antibiotic-like action of plant viruses," Experimentia, 1947, 3:70-71.
Haenni et al., "Structure chimique des aspergillomarasmines A et B," Helv. Chim. Acta, 1965, 48:729-750.
Hernandez Valladares et al., "Zn(II) dependence of the Aeromonas hydrophila AE036 metallo-beta-lactamase activity and stability," Biochemistry, 1997, 36:11534-11541.

Holmquist et al., "A continuous spectrophotometric assay for angiotensin converting enzyme," Anal Biochem, 1979, 95:540-548.
Lee et al., "A Practical Synthesis of Nitrocefin," J. Org. Chem., 2005, 70:367-369.
Matsuura et al., "Pharmacological profiles of aspergillomarasmines as endothelin converting enzyme inhibitors," Jap. J. Ppharmacol., 1993, 63:187-193.
Patel et al., "Stormy waters ahead: global emergence of carbapenemases," Frontiers Microbiol., 2013, 4:48(1-17).
Pillai et al., "Antimocrobial Combinations," G. M. In Antibiotics in Laboratory Medicine (ed V. Lorian), 2005, 365-440, Williams & Wilkins, Philadelphia.
Pitout et al., "Extended-spectrum beta-lactamase-producing Enterobacteriaceae: an emerging public-health concern," Lancet Infect. Dis., 2008, 8:159-166.
Ricci et al., "The Barn machine: a molecular cooper," Biochim. Biophys. Acta, 2012, 1818:1067-1084.
Robert et al., Two new natural phytotoxins: aspergillomarasmine A and B and their relation to lycomarasmine and its derivatives, Bulletin de la Societe Chimique de France, 1962, 187-188.
Shlaes, D. M., "New beta-lactam-beta-lactamase inhibitor combinations in clinical development," Ann. NY Acad. Sci., 2013, 1277:105-114.
Yigit et al., "Novel carbapenem-hydrolyzing beta-lactamase, KPC-1, from a carbapenem-resistant strain of Klebsiella pneumoniae," Antimicrob. Agents nd Chemother., 2001, 45:1151-1161.
Zhang et al., "A Simple Statistical Parameter for Use in Evaluation and Validation of High Throughput Screening Assays," J. Biomol. Screen., 1999. 4:67-73.

* cited by examiner

INHIBITORS OF METALLO-β-LACTAMASE-ENZYMES

RELATED APPLICATIONS

This application is a National Stage of co-pending International Application No. PCT/CA2014/050434, filed May 7, 2014, which claims the benefit of priority of U.S. Provisional Patent Application No. 61/820,277, filed on May 7, 2013, the contents of both of which are herein incorporated in their entirety by reference.

FIELD

The present application relates to combination treatments for bacterial infections. For example, the application relates to the use of one or more antibiotics and one or more compounds of Formula I as defined herein, for treatment of a metallo-β-lactamase-expressing bacterial infection or a disease, disorder or condition arising from a metallo-β-lactamase-expressing bacterial infection.

BACKGROUND

The β-lactams (penicillins, cephalosporins, carbapenems and monobactams) are one of the most important and frequently used classes of antibiotics in medicine, in particular in the treatment of serious Gram-negative infections. Since the clinical introduction of penicillins and cephalosporins over 60 years ago, the emergence of β-lactamases, enzymes that hydrolyse the β-lactam ring that is involved in the cell-killing activity of these compounds, has been an ongoing clinical problem[1]. Antibiotic resistance has intensified medicinal chemistry efforts to broaden antibacterial spectrum while shielding the core β-lactam scaffold from β-lactamase-catalyzed hydrolysis. The result has been multiple generations of β-lactams with improved efficacy and tolerance to existing β-lactamases. However, pathogenic bacteria have in turn evolved further resistance mechanisms primarily by acquiring new or modified β-lactamases. This is typified by the emergence of extended spectrum β-lactamases that inactivate many of the latest generation cephalosporins and penicillins (but not carbapenems)[2]. Consequently, the past two decades have seen significant increases in the utilization of carbapenems such as imipenem and meropenem. Predictably, this increase in carbapenem consumption has been accompanied by the emergence of carbapenem-resistant Gram-negative bacteria[3]. In particular, carbapenem-resistant Enterobacteriaceae (CRE) is a growing crisis across the globe[4] as witnessed by recent outbreaks in Chicago[5] and British Columbia[6].

Carbapenemases, β-lactamases that inactivate carbapenems, can be divided into two categories based on their mechanism of β-lactam ring hydrolysis. The first deploy an active site Serine residue that covalently attacks the β-lactam ring e.g. KPC and OXA-48 types[7]. The second are metallo-β-lactamases (MBLs) that use $Zn^{2+}$ atoms to activate a nucleophilic water molecule that opens the ring e.g. Verona integron-encoded metallo-β-lactamase (VIM) and New Dehli metallo-β-lactamase (NDM) types[8]. Several inhibitors of Ser β-lactamases are clinically available as co-drugs where the inhibitor is formulated with a β-lactam antibiotic in order to overcome resistance (e.g. clavulanic acid-amoxicillin, tazobactam-piperacillin, sulbactam-ampicillin and the more recent Ser β-lactamase inhibitor avibactarn, which is in phase III clinical trials paired with various cephalosporins)[9]. Despite ongoing efforts[10,11] there are no equivalent inhibitors for MBLs in the clinic for practical and technical reasons. First, until recently, MBL-derived CRE was not thought to be a major clinical problem and its rapid increase has outpaced MBL-inhibitor development. Second, the development of a single inhibitor to neutralise key clinically important MBL, such as VIM and NDM has been deemed too technically challenging, and overcoming in vivo toxicity associated with cross reactivity with human metallo-enzymes has been a concern. With the recent emergence of MBLs as a significant clinical threat, a potent and safe inhibitor of MBLs particularly against VIM and NDM would greatly benefit infectious disease management.

Aspergillomarasmines A and B are fungus-derived molecules that were discovered and reported in the early 1960s[12,13]. These molecules were evaluated in the 1980s as inhibitors of angiotensin-converting enzyme (ACE)[14] and in the early 1990s as a pre-clinical candidate for the inhibition of activation of human endothelin[15,16], a peptide that modulates blood vessel muscle contraction. This previous work demonstrated that AM-A was well-tolerated and had low toxicity in mice ($LD_{50}$ 159.8 mg/kg, i.v. compared to EDTA at 28.5 mg/kg) and had no effect on mean atrial blood pressure[17]. Another study reporting that AM-A has an $LD_{50}$ of 250 mg/kg i.v. while AM-B has an $LD_{50}$ of 660 mg/kg i.v. in rats[14].

Lycomarasmine is also a fungal derived molecule that was first reported in 1947[18].

SUMMARY

In the present application the compound aspergillomarasmine A (AM-A), and certain analogs and derivatives, are disclosed as potentiators of β-lactam antibiotics.

Accordingly, in an embodiment, the present application includes a pharmaceutical composition comprising:
one or more β-lactam antibiotics; and
one or more compounds of Formula I:

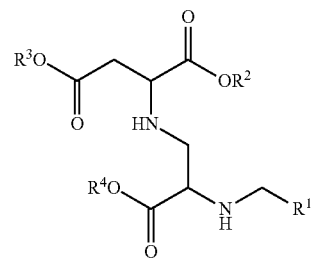

wherein
$R^1$ is selected from $C(O)OR^5$, $C(O)NHR^5$ and $CH(NH_2)C(O)OR^5$;
$R^2$, $R^3$, $R^4$ and $R^5$ are independently selected from H, $C_{1-24}$alkyl, $C_{1-6}$alkylene$C_{6-10}$aryl, $C_{1-6}$alkylene$C_{3-10}$cycloalkyl, $C_{1-6}$alkylene$C_{3-10}$heterocycloalkyl and $C_{1-6}$alkylene-OC(O)$C_{1-6}$alkyl; and
n, m and p are independently selected from 1 and 2;
or a pharmaceutically acceptable salt and/or solvate thereof, and
the one or more β-lactam antibiotics and one or more compounds of Formula I are present in amounts that are effective to treat a bacterial infection, or a disease, disorder or condition arising from a bacterial infection.

In another embodiment, the present application includes a method of treating a bacterial infection comprising administering, to a subject in need thereof, an effective amount of one or more β-lactam antibiotics in combination with an effective amount of one or more compounds of Formula I:

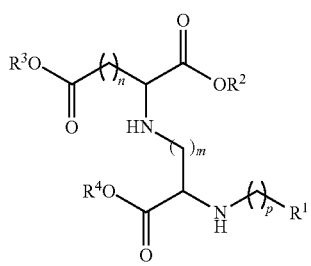

wherein
$R^1$ is selected from $C(O)OR^5$, $C(O)NHR^5$ and $CH(NH_2)C(O)OR$;
$R^2$, $R^3$, $R^4$ and $R^5$ are independently selected from H, $C_{1-24}$alkyl, $C_{1-6}$alkylene$C_{6-10}$aryl, $C_{1-6}$alkylene$C_{3-10}$cycloalkyl, $C_{1-6}$alkylene$C_{3-10}$heterocycloalkyl and $C_{1-6}$alkylene-$OC(O)C_{1-6}$alkyl; and
n, m and p are independently selected from 1 and 2;
or a pharmaceutically acceptable salt and/or solvate thereof.

In another embodiment, the present application includes a method of treating or preventing a disease, disorder or condition arising from a bacterial infection in a subject comprising administering, to the subject, an effective amount of one or more β-lactam antibiotics in combination with an effective amount of one or more compounds of Formula I as defined above, or a pharmaceutically acceptable salt and/or solvate thereof.

In another embodiment, the present application includes a method of improving the efficacy of a β-lactam antibiotic for treating a bacterial infection comprising administering, to a subject in need thereof, an effective amount of one or more compounds of Formula I as defined above, or a pharmaceutically acceptable salt and/or solvate thereof, in combination with the antibiotic, as well as a method of improving the efficacy of a β-lactam antibiotic for treating a disease, disorder or condition arising from a bacterial infection comprising administering, to a subject in need thereof, an effective amount of one or more compounds of Formula I as defined above, or a pharmaceutically acceptable salt and/or solvate thereof, in combination with the antibiotic.

The present application also includes a method of treating bacterial infections in animals or humans which comprises administering the defined β-lactamase inhibitor compound in combination with a pharmaceutically acceptable β-lactam antibiotic in an amount which is effective for treating a bacterial infection. The present application also includes a method of treating metallo-β-lactamase-expressing Enterobacteriaceae, in particular *Klebsiella pneumoniae* related diseases in animal and human subjects comprising administering to the subject an effective amount of either AM-A, or any active AM-A analog or derivative, in combination with an effective amount of a β-lactam antibiotic, specifically a carbapenem antibiotic.

The present application also includes an antibacterial combination comprising an effective amount of a fungal natural product, aspergillomarasmine A or any active analogues thereof, and a β-lactam antibiotic. In an embodiment, the fungal natural product is aspergillomarasmine A or any active analogues thereof, and the lactam antibiotic is selected from the group consisting of penicillin, cephalosporin, monobactam and carbapenem antibiotics. In a further embodiment, the fungal natural product is aspergillomarasmine A or any active analogues thereof, and the β-lactam antibiotic is a carbapenem. In a further embodiment, the β-lactam antibiotic is meropenem.

It is an embodiment of the application that the antibacterial combination is formulated into a pharmaceutical dosage form. In a further embodiment of the application, the antibacterial combination is for use in a method of treatment and/or preventing a bacterial infection in an individual, said infection being caused by bacteria producing one or more metallo-β-lactamase enzymes, the method comprising administration of the combination to a human or animal subject.

In an embodiment, the bacterial infection is an infection of at least one metallo-β-lactamase (MBL)-expressing bacterium, and the disease, disorder or condition arising from a bacterial infection is a disease, disorder or condition arising from at least one MBL-expressing bacterial infection.

In an embodiment, the bacterium causing infection is selected from *Staphylococcus aureus, Staphylococcus epidermidis* and other coagulase-negative *staphylococci, Streptococcus pyogenes, Streptococcus pneumoniae, Streptococcus agalactiae, Enterococcus* species, *Corynebacterium diphtheriae, Listeria monocytogenes, Bacillus anthracis, Neisseria meningitidis, Neisseria gonorrhoeae, Moraxella catarrhalis, Vibrio cholerae*, and *Campylobacter jejuni*.

In an embodiment, the bacterium causing infection is selected from selected from Enterobacteriaceae (includes: *Escherichia, Salmonella, Klebsiella, Enterobacter*), *Pseudomonas aeruginosa, Acinetobacter* species, *Haemophilus influenzae, Clostridium tetani, Clostridium botulinum, Bacteroides* species, *Prevotella* species, *Porphyromonas* species, *Fusobacterium* species, *Mycobacterium tuberculosis*, and *Mycobacterium leprae*.

In an embodiment, the bacterium causing infection is from the Enterobacteriaceae family.

In an embodiment, the bacterium causing infection is *Klebsiella pneumonia*.

The present application also includes a cell-based screening assay comprising bacterial cells that express a bacterial resistance gene, wherein the cells are modified to be deficient in one or more of (i) genes encoding proteins that block the entry of molecules into the cells and (ii) genes encoding proteins that facilitate efflux of molecules out of the cells.

Also included in the present application is a method of identifying compounds that treat antibiotic resistance comprising:
(a) contacting one or more compounds with bacterial cells that express a bacterial resistance gene, wherein the cells are modified to be deficient in one or more of (i) genes encoding proteins that block the entry of molecules into the cells and (ii) genes encoding proteins that facilitate efflux of molecules out of the cells, and wherein the one or more compounds are contacted with the cells in the presence of an antibiotic that is susceptible to a protein encoded by the bacterial resistance gene; and
(b) identifying compounds that inhibit growth of the bacterial cells as compounds that treat antibiotic resistance.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

DRAWINGS

Figure 2:
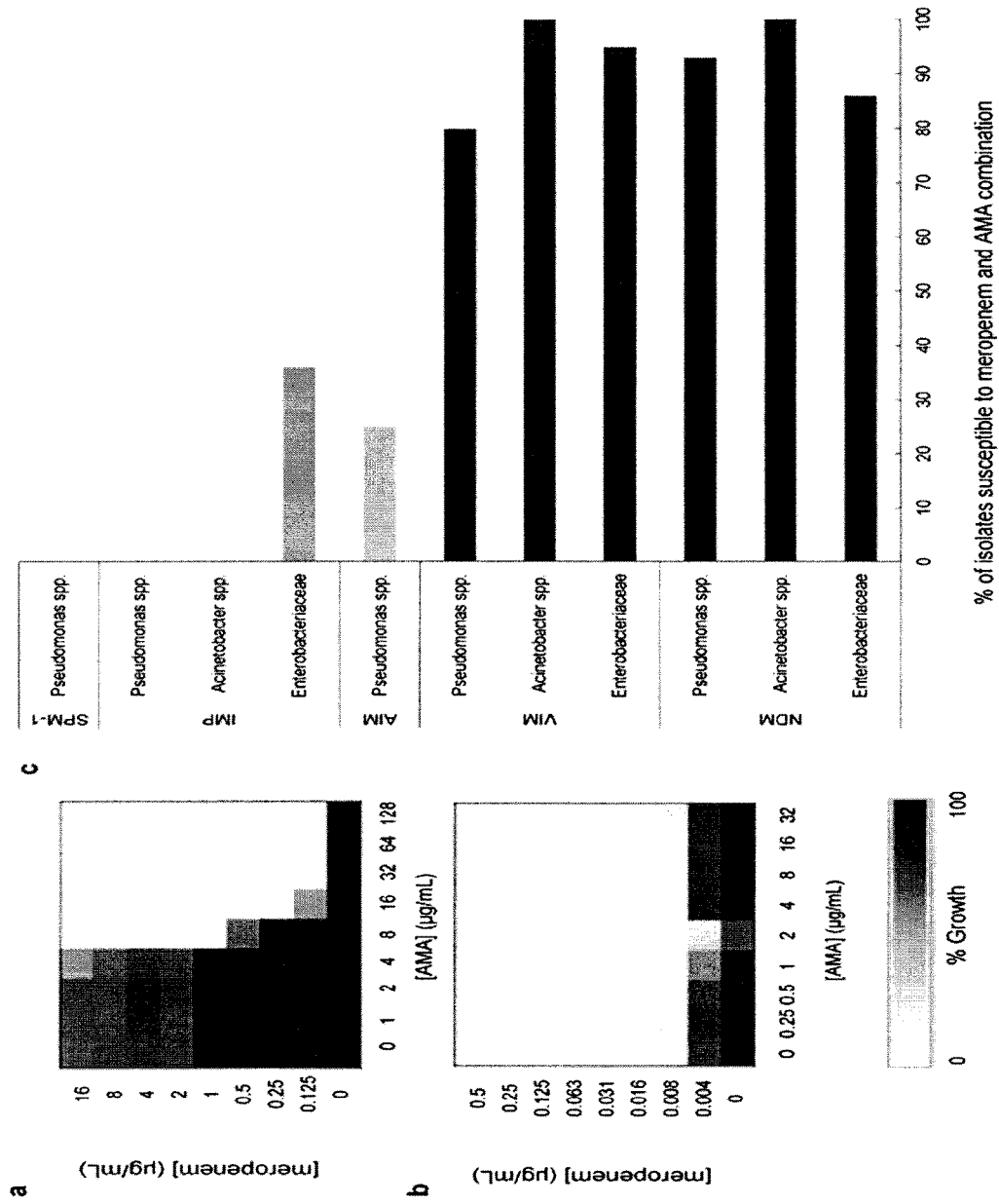

The embodiments of the application will now be described in greater detail with reference to the attached drawings in which:

FIG. 1 shows that AM-A (depicted in (a)) (b) inhibits NDM-1 (●) ($IC_{50}$ 4.0±1.0 M) and VIM-2 (○) ($IC_{50}$ of 9.6±2.4 μM) and the activity of OXA-48 (■) was unaffected by AM-A; (c) removal of AM-A via PD10 column does not restore NDM-1 activity, confirming irreversible inactivation; (d) addition of excess $ZnSO_4$ restores activity post-inactivation; (e) the rate of inactivation of NDM-1 and VIM-2 is saturable with [AM-A]; and (f) ICP-MS confirms depletion of Zn from NDM-1. Error bars denote standard deviation of three replicates FIG. 2 shows (a, b) microdilution checkerboard analysis showing the combined effect of AM-A and meropenem selectively against CRE (a, *K. pneumoniae* N11-2218 MIC meropenem=32 μg/ml) but not a carbapenem sensitive strain (b, *E. coli* BW25113 MIC=0.008-0.016 μg/ml); (c) VIM- and NDM-expressing Gram negative pathogens were highly susceptible to meropenem/AM-A combination (respectively 2 μg/ml and 8 μg/ml) while AIM-, IMP-, and SPM-1-expressing isolates remained resistant.

Figure 3:
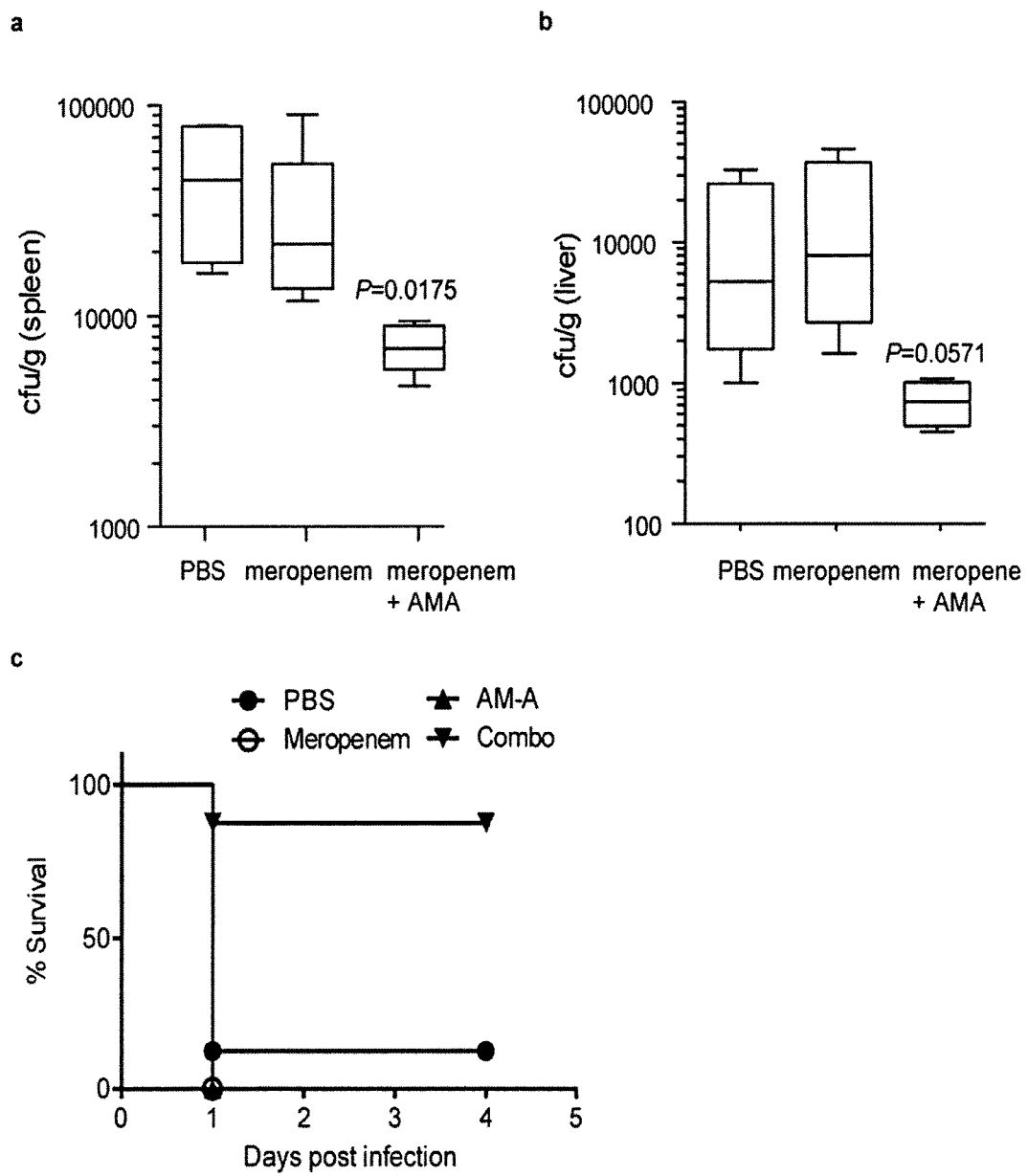

FIG. 3 shows treatment results for CD-1 mice given a lethal dose of *K. pneumoniae* N11-2218 (meropenem MIC 32 μg/mL) by i.p. injection: (a, b) Groups of mice were treated with a single dose of meropenem (10 mg/kg), a combination of meropenem (10 mg/kg)+AM-A (10 mg/kg), or PBS by s.c. injection. Injection and bacterial load in the spleen (a) and liver (b) was determined by selective plating. Data are the means with standard error from two separate experiments. (c) Mice were treated with a single dose of meropenem (10 mg/kg), a combination of meropenem (10 mg/kg)+AM-A (30 mg/kg) or PBS by s.c. injection

DETAILED DESCRIPTION

I. Definitions

Unless otherwise indicated, the definitions and embodiments described in this and other sections are intended to be applicable to all embodiments and aspects of the present application herein described for which they are suitable as would be understood by a person skilled in the art.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise. For example, an embodiment including " a β-lactam antibiotic" should be understood to present certain aspects with one β-lactam antibiotic or two or more additional β-lactam antibiotics.

In embodiments comprising an "additional" or "second" component, such as an additional or second β-lactam antibiotic, the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present.

The term "bacterial infection" as used herein refers to an invasion of cells or bodily tissues by a foreign, undesirable bacteria. In an embodiment, the bacterial infection is a metallo-β-lactamase-expressing infection.

The term "metallo-β-lactamase-expressing infection" as used herein refers to an invasion of cells or bodily tissues by a bacterium that expresses a metallo-β-lactamase.

The term "β-lactam antibiotic" as used herein refers to a class of antibiotics having a β-lactam ring in their molecular structures. This includes, for example, penicillin derivatives (penems), cephalosporins (cephems), monobactams and carbapenems. Most β-lactam antibiotics work by inhibiting cell wall biosynthesis in the bacterial organism and are the most widely used group of antibiotics.

The term "alkyl" as used herein, whether it is used alone or as part of another group, means straight or branched chain, saturated hydrocarbyl groups. For example, the term $C_{1-24}$alkyl means an alkyl group having 1, 2, 3, 4, 5, 6, 7, 8, 9, 11, 12, 13, 14, 15, 16, 17, 18, 19, 20, 21, 22, 23 or 24 carbon atoms.

The term "alkylene" as used herein means straight or branched chain, saturated hydrocarbyl group, that is a saturated carbon chain that contains substituents on two of its ends. For example, the term $C_{1-6}$alkylene means an alkylene group having 1, 2, 3, 4, 5 or 6 carbon atoms.

The term "cycloalkyl," as used herein, whether it is used alone or as part of another group, means saturated alkyl groups having at least one cyclic ring. For example, the term $C_{3-10}$cycloalkyl means a cycloalkyl group having 3, 4, 5, 6, 7, 8, 9 or 10 carbon atoms.

The term "aryl" or "aromatic" as used herein, whether it is used alone or as part of another group, refers to cyclic groups that contain at least one aromatic ring. In an embodiment of the application, the aryl group contains from 6 or 10, such as phenyl, naphthyl or indanyl.

The term "heterocycloalkyl" as used herein, whether it is used alone or as part of another group, refers to a non-aromatic, monocyclic ring or a polycyclic ring system containing 5, 6, 7, 8, 9, or 10 atoms, of which one or more, for example 1 to 6, 1 to 5, 1 to 4, or 1 to 3, of the atoms are a heteromoiety selected from O, S, NH and $NC_{1-6}$alkyl, with the remaining atoms being C, CH or $CH_2$. Heterocycloalkyl groups are either saturated or unsaturated (i.e. contain one or more double bonds) and may contain more than one ring. When a heterocycloalkyl group contains more than one ring, the rings may be fused, bridged, spiro connected or linked by a single bond.

A first ring group being "fused" with a second ring group means the first ring and the second ring share at least two adjacent atoms there between.

A first ring group being "bridged" with a second ring group means the first ring and the second ring share at least two non-adjacent atoms there between.

A first ring group being "spiro connected" with a second ring group means the first ring and the second ring share one atom there between.

The term "aspergillomarasime A" or "AM-A" as used herein refers to a compound of the formula:

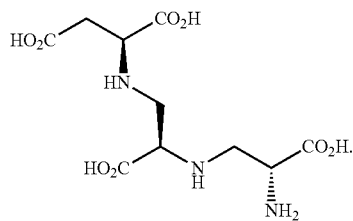

The term "aspergillomarasime B" or "AM-B" as used herein refers to a compound of the formula:

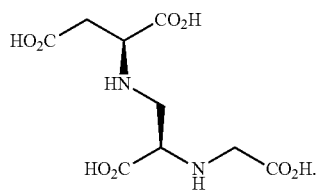 [SMILES: O=C(O)CN[C@H](CN[C@@H](CC(=O)O)C(=O)O)C(=O)O]

The term "lycomarasmine" as used herein refers to a compound of the formula:

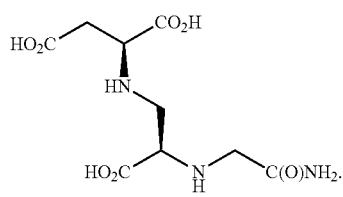

The term "pharmaceutically acceptable salt" means an acid addition salt or a basic addition salt suitable for, or compatible with, the treatment of subjects.

The term "pharmaceutically acceptable salts" embraces salts commonly used to form addition salts of free acids or free bases. The nature of the salt is not critical, provided that it is pharmaceutically-acceptable. Suitable pharmaceutically acceptable acid addition salts are prepared from an inorganic acid or an organic acid. Examples of such inorganic acids include, without limitation, hydrochloric, hydrobromic, hydroiodic, nitric, carbonic, sulfuric and phosphoric acid. Examples of appropriate organic acids include, for example, aliphatic, cycloaliphatic, aromatic, arylaliphatic, heterocyclic, carboxylic and sulfonic classes of organic acids, examples of which include, without limitation, formic, acetic, propionic, succinic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactic, and galacturonic acid. Suitable pharmaceutically-acceptable base addition salts include, but are not limited to, metallic salts made from aluminum, calcium, lithium, magnesium, potassium, sodium and zinc or organic salts made from N,N'-dibenzylethylenediamine, chloroprocaine, choline, diethanolamine, ethylenediamine, N-methylglucamine, lysine and procaine.

The formation of a desired compound salt is achieved using standard techniques. For example, the neutral compound is treated with an acid or base in a suitable solvent and the formed salt is isolated by filtration, extraction or any other suitable method.

The term "solvates" as used herein refers to complexes formed between a compound and a solvent from which the compound is precipitated or in which the compound is made. Accordingly, the term "solvate" as used herein means a compound, or a salt a compound, wherein molecules of a suitable solvent are incorporated in the crystal lattice. Examples of suitable solvents are ethanol, water and the like. When water is the solvent, the molecule is referred to as a "hydrate". The formation of solvates will vary depending on the compound and the solvate. In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art.

The term "pharmaceutically acceptable solvate" means a solvate suitable for, or compatible with, the treatment of subjects. For pharmaceutically acceptable solvates, a suitable solvent is physiologically tolerable at the dosage used or administered.

The expression "disease, disorder or condition arising from a bacterial infection" as used herein refers to any disease, disorder or condition that is directly or indirectly caused by the presence of a bacterial infection in a subject.

The term "subject" as used herein includes all members of the animal kingdom including mammals.

The term "pharmaceutical composition" as used herein refers to a composition of matter for pharmaceutical use.

The term "pharmaceutically acceptable" means compatible with the treatment of subjects, for example, mammals such as equines and humans.

The term "parenteral" as used herein means taken into the body or administered in a manner other than through the gastrointestinal tract.

The term "administered" as used herein means administration of an effective amount of a compound, including the antibiotic and compound of Formula I, or a salt and/or solvate thereof, to a cell either in cell culture or in a subject.

As used herein, the term "effective amount" or "therapeutically effective amount" means an amount effective, at dosages and for periods of time necessary to achieve a desired result. For example, in the context of treating a bacterial infection, or a disease, disorder or condition arising from a bacterial infection, an effective amount of the antibiotic and/or compound of Formula I, or a salt and/or solvate thereof, is an amount that, for example, reduces the bacterial infection compared to the bacterial infection without administration of the antibiotic and the compound of Formula I, or a salt and/or solvate thereof. Further, in the context of improving the efficacy of an antibiotic for the treatment of a bacterial infection or a disease, disorder or condition arising from a bacterial infection an effective amount of the compound of Formula I, or a salt and/or solvate thereof, is, for example, an amount that, for example, reduces the bacterial infection compared to the reduction of the bacterial infection with administration of the antibiotic alone. By "reducing the infection", it is meant, for example, reducing the amount of the infectious agent in the subject and/or reducing the symptoms of the infection. Effective amounts may vary according to factors such as the disease state, age, sex and/or weight of the subject. The amount of a given compound or composition that will correspond to such an amount will vary depending upon various factors, such as the given compound or composition, the pharmaceutical formulation, the route of administration, the type of condition, disease or disorder, the identity of the subject being treated, and the like, but can nevertheless be routinely determined by one skilled in the art.

The terms "to treat", "treating" and "treatment" as used herein and as is well understood in the art, means an approach for obtaining beneficial or desired results, including clinical results. Beneficial or desired clinical results include, but are not limited to, diminishment of extent of bacterial infection, stabilization (i.e. not worsening) of the state of the bacterial infection, preventing spread of the bacterial infection, delay or slowing of infection progression, amelioration or palliation of the bacterial infectious state, diminishment of the reoccurrence of bacterial infection, diminishment, stabilization, alleviation or amelioration of one or more diseases, disorders or conditions arising from the bacterial infection, diminishment of the reoccurrence of one or more diseases, disorders or conditions arising from the bacterial infection, and remission of the bacterial infection and/or one or more symptoms or conditions arising from the bacterial infection, whether partial or total, whether detectable or undetectable. "To treat", "treating" and "treatment" can also mean prolonging survival as compared to expected survival if not receiving treatment. "To treat", "treating" and "treatment" as used herein also include prophylactic treatment. For example, a subject with an early bacterial infection is treated to prevent progression, or alternatively a subject in remission is treated to prevent recurrence.

"Palliating" an infection, disease, disorder and/or condition means that the extent and/or undesirable clinical manifestations of an infection, disease, disorder and/or condition are lessened and/or time course of the progression is slowed or lengthened, as compared to not treating the infection, disease, disorder and/or condition.

The term "prevention" or "prophylaxis" and the like as used herein refers to a reduction in the risk or probability of a subject becoming afflicted with a bacterial infection and/or a disease, disorder and/or condition arising from a bacterial infection or manifesting a symptom associated with a bacterial infection and/or a disease, disorder and/or condition arising from a bacterial infection.

When used, for example, with respect to the methods of treatment, uses, compositions and kits of the application, a subject, for example a subject "in need thereof" is a subject who has been diagnosed with, is suspected of having, may come in to contact with, and/or was previously treated for a bacterial infection or a disease, disorder or condition arising from a bacterial infection.

II. Methods and Uses

A cell-based screen for inhibitors of the NDM-1 metallo-β-lactamase using a collection of natural product extracts derived from environmental microorganisms was performed. To increase the sensitivity of the screen to MBL inhibitor discovery a test strain of *Escherichia coli* BW25113 in which the bamB and tolC genes were independently deleted (*E. coli* BW25113ΔbamBΔtolC) was generated. BamB is involved in outer membrane porin assembly and disruption results in increased permeability to small molecules[19] and TolC is a part of the tripartite small molecule efflux systems such as AcrA-AcrB-TolC that serve to actively eliminate small molecules from the cell[20]. Therefore, *E. coli* BW25113ΔbamBΔtolC increases the sensitivity of the screen to discovery of "hits". This strain was further modified by integrating the $bla_{NDM-1}$ β-lactamase gene under control of the pLac promoter into the chromosome [*E. coli* BW25113ΔbamBΔtolCΔaraDAB::pLac($bla_{NDM-1}$)]. This strain was screened in the presence of a sub-lethal concentration of meropenem (of the minimum inhibitory concentration 0.125 μg/mL) in combination with ~500 natural product extracts.

In an exemplary embodiment of the present application, the screen generated a reproducible hit from an extract of a strain of *Aspergillus versicolor* (as identified by 18S rRNA gene sequence) with excellent ability to restore meropenem antibiotic activity against the *E. coli* screening strain. The selectivity of the extract to neutralise NDM-1 activity in vitro was confirmed using purified enzyme and the colorimetric β-lactamase substrate nitrocefin and with the carbapenem drug meropenem. Activity-guided purification of the active compound from the fermentation broth of *A. versicolor* and subsequent detailed chemical characterization identified the MBL inhibitor as aspergillomarasmine A (AM-A).

Accordingly, in an embodiment, the present application includes a method of treating a bacterial infection comprising administering, to a subject in need thereof, an effective amount of one or more β-lactam antibiotics in combination with an effective amount of one or more compounds of Formula I:

I 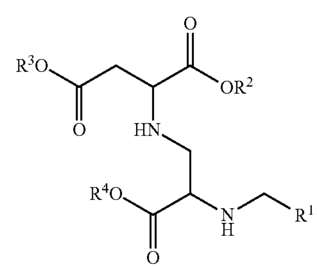 wherein $R^1$ is selected from $C(O)OR^5$, $C(O)NHR^5$ and $CH(NH_2)C(O)OR^5$;

$R^2$, $R^3$, $R^4$ and $R^5$ are independently selected from H, $C_{1-24}$alkyl, $C_{1-6}$alkylene$C_{6-10}$aryl, $C_{1-6}$alkylene$C_{3-10}$cycloalkyl, $C_{1-6}$alkylene$C_{3-10}$heterocycloalkyl and $C_{1-6}$alkylene-OC(O)$C_{1-6}$alkyl; and n, m and p are independently selected from 1 and 2;

or a pharmaceutically acceptable salt and/or solvate thereof.

The present application also includes a use of a β-lactam antibiotic in combination with one or more compounds of Formula I as defined above, or a pharmaceutically acceptable salt and/or solvate thereof, for treating a bacterial infection in a subject; a use of a β-lactam antibiotic in combination with one or more compounds of Formula I as defined above, or a pharmaceutically acceptable salt and/or solvate thereof, for preparation of a medicament for treating a bacterial infection in a subject; and a β-lactam antibiotic and one or more compounds of Formula I as defined above, or a pharmaceutically acceptable salt and/or solvate thereof, for use to treat a bacterial infection in a subject.

In another embodiment, the present application includes a method of treating or preventing a disease, disorder or condition arising from a bacterial infection in a subject comprising administering, to the subject, an effective amount of one or more β-lactam antibiotics in combination with an effective amount of one or more compounds of Formula I as defined above, or a pharmaceutically acceptable salt and/or solvate thereof.

The present application also includes a use of a β-lactam antibiotic in combination with of one or more compounds of Formula I as defined above, or a pharmaceutically acceptable salt and/or solvate thereof, for treating a disease, disorder or condition arising from a bacterial infection in a subject; a use of a β-lactam antibiotic in combination with of one or more compounds of Formula I as defined above, or a pharmaceutically acceptable salt and/or solvate thereof, for preparation of a medicament for treating disease, disorder or condition arising from a bacterial infection in a subject; and a β-lactam antibiotic and of one or more compounds of Formula I as defined above, or a pharmaceutically acceptable salt and/or solvate thereof, for use to treat a disease, disorder or condition arising from a bacterial infection in a subject.

In another embodiment, the present application includes a method of improving the efficacy of a β-lactam antibiotic for treating a bacterial infection comprising administering, to a subject in need thereof, an effective amount of one or more compounds of Formula I as defined above, or a pharmaceutically acceptable salt and/or solvate thereof in combination with the antibiotic.

The present application also includes a use of one or more compounds of Formula I as defined above, or a pharmaceutically acceptable salt and/or solvate thereof, for improving the efficacy of a β-lactam antibiotic for treating a bacterial infection in a subject; a use of of one or more compounds of Formula I as defined above, or a pharmaceutically acceptable salt and/or solvate thereof, for preparation of a medicament for improving the efficacy of a β-lactam antibiotic for treating a bacterial infection in a subject; and of one or more compounds of Formula I as defined above, or a pharmaceutically acceptable salt and/or solvate thereof, for use to improve the efficacy of a β-lactam antibiotic to treat a bacterial infection in a subject.

The present application also includes a method of improving the efficacy of a β-lactam antibiotic for treating a disease, disorder or condition arising from a bacterial infection comprising administering, to a subject in need thereof, an effective amount of one or more compounds of Formula I as defined above, or a pharmaceutically acceptable salt and/or solvate thereof.

The present application also includes a use of one or more compounds of Formula I as defined above, or a pharmaceutically acceptable salt and/or solvate thereof, for improving the efficacy of a β-lactam antibiotic for treating a disease, disorder or condition arising from a bacterial infection in a subject; a use of one or more compounds of Formula I as defined above, or a pharmaceutically acceptable salt and/or solvate thereof, for preparation of a medicament for improving the efficacy of a β-lactam antibiotic for treating a disease, disorder or condition arising from a bacterial infection in a subject; and one or more compounds of Formula I as defined above, or a pharmaceutically acceptable salt and/or solvate thereof, for use to improve the efficacy of a β-lactam antibiotic for treating a disease, disorder or condition arising from a bacterial infection in a subject.

In an embodiment, the bacterial infection is an infection of at least one metallo-β-lactamase (MBL)-expressing bacterium, and the disease, disorder or condition arising from a bacterial infection is a disease, disorder or condition arising from at least one MBL-expressing bacterial infection. In an embodiment, the MBL is an IMP-type, a Verona integron-encoded metallo-β-lactamase (VIM) or a New Delhi metallo-β-lactamase (NDM). In a further embodiment, the MBL is VIM or NDM.

In an embodiment, the bacterial infection is an infection of at least one carbapenem-resistant Gram-negative bacteria.

In an embodiment, the bacterial infection is an infection of at least one bacterium belonging to the family Enterobacteriaceae, *Acinetobacter, Pseudomonas*.

In an embodiment the Enterobacteriaceae bacterium is a *Klebsiella* species, such as *Klebsiella pneumonia* or *Escherichia coli*. In another embodiment, the *Pseudomonas* bacterium is *Pseudomonas aeruginosa*.

In an embodiment, the bacterium causing infection is selected from *Staphylococcus aureus, Staphylococcus epidermidis* and other coagulase-negative *staphylococci, Streptococcus pyogenes, Streptococcus pneumoniae, Streptococcus agalactiae, Enterococcus* species, *Corynebacterium diphtheriae, Listeria monocytogenes, Bacillus anthracis, Neisseria meningitidis, Neisseria gonorrhoeae, Moraxella catarrhalis, Vibrio cholerae*, and *Campylobacter jejuni*.

In an embodiment, the bacterium causing infection is selected from selected from Enterobacteriaceae (includes: *Escherichia, Salmonella, Klebsiella, Enterobacter*), *Pseudomonas aeruginosa, Acinetobacter* species, *Haemophilus influenzae, Clostridium tetani, Clostridium botulinum, Bacteroides* species, *Prevotella* species, *Porphyromonas* species, *Fusobacterium* species, *Mycobacterium tuberculosis*, and *Mycobacterium leprae*.

In an embodiment, the bacterium causing infection is from the Enterobacteriaceae family.

In an embodiment, the bacterium causing infection is *Klebsiella pneumoniae*.

The diseases, disorders or conditions arising from a bacterial infection include all such pathogeneses that are common to infections of MBL-expression bacteria. These are well known to those skilled in the art. Some of the more common examples are listed below for the better known MBL-expressing bacteria, however, a person skilled in the art would appreciate that these lists are non-exhaustive and many of the diseases, disorders and conditions listed for one MBL-expression bacterium will be common to other MBL-expressing bacteria.

In an embodiment, the disease, disorder or condition arising from a bacterial infection, such as an infection of *K. pneumoniae*, is for example, but not limited to, pneumonia (for example bronchopneumonia or bronchitis), thrombophlebitis, urinary tract infection (UTI), cholecystus, diarrhea, upper respiratory tract infection, lower biliary tract infection, wound infection, surgical wound infection, osteomyelitis, meningitis, bacteremia, septicemia, sepsis, septic shock, rhinoscleroma, ozena, ankylosing spondylitis, destructive changes to human lungs via inflammation and hemorrhage with cell death (necrosis), lung abscesses, cavitations, empyemas, or ural adhesions, or a combination thereof.

In an embodiment, the disease, disorder or condition arising from bacterial infection, such as an infection of Pseudomonas aeruginosa, is for example, but not limited to, cystic fibrosis, pneumonia, bacteremia, endocarditis, meningitis, brain abscesses, septic shock, UTI, gastrointestinal infection (e.g. diarrhea, enteritis, or enterocolitis), skin infections (e.g. ecthyma gangrenosum), soft tissue infections, infections of burn injuries, infections of the outer ear, bacterial keratitis, endophthalmitis, infections due to the presence of a medical device, infections due to hospitalization, infections caused by low water quality, post-operative infections, or osteomyelitis, or a combination thereof.

In an embodiment, the disease, disorder or condition arising from bacterial infection, such as an infection of Escherichia coli, is for example, but not limited to, enteric infections (e.g. diarrhea), intra-abdominal infections, cholecystitus, bacteremia, cholangitis, UTI, meningitis, pneumonia, septic arthritis, endophthalmitis, suppurative thyroiditis, osteomyelitis, endocarditis, skin infections or soft tissue infections, or a combination thereof.

In an embodiment, the subject is a human. In a further embodiment, the subject is an animal, such as a companion animal or livestock.

The one or more antibiotics are selected from any antibiotic which treats metallo-β-lactamase-expressing bacterial infections. In an embodiment, one or more antibiotics are β-lactam antibiotics. In an embodiment, the β-lactam antibiotic is selected from penicillin derivatives (penems), cephalosporins (cephems), monobactams and carbapenems. In an embodiment, the β-lactam antibiotic is selected from imipenem, ertapenem, meropenem, doripenem, biapenem, panipenem, ticarcillin, ampicillin, amoxicillin, carbenicillin, piperacillin, azlocillin, mezlocillin, ticarcillin, cefoperazone, cefotaxime, ceftriaxone and ceftazidime.

In another embodiment, the one or more antibiotics are carbapenem antibiotics. In an embodiment, the carbapenem antibiotic is selected from meropenem, biapenm, doripenem, ertapenem, panipenem and imipenem.

In an embodiment, the compound of Formula I has the following relative stereochemistry:

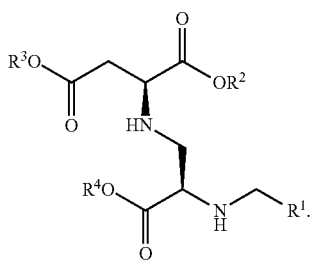

In an embodiment, $R^2$, $R^3$, $R^4$ and $R^5$ are each, H. In an embodiment, and $R^2$, $R^3$, $R^4$ and $R^5$ are independently selected from $C_{1-18}$alkyl, $C_{1-4}$alkyleneC$_{5-6}$heterocycloalkyl and $C_{1-4}$alkylene-OC(O)$C_{1-6}$alkyl. In an embodiment, $R^2$, $R^3$, $R^4$ and $R^5$ are the same and are selected from $C_{1-18}$alkyl, $C_{1-4}$alkyleneC$_{5-6}$heterocycloalkyl and $C_{1-4}$alkylene-OC(O)$C_{1-6}$alkyl.

In an embodiment, when at least one of $R^2$, $R^3$, $R^4$ and $R^5$ is other than H, the compound of Formula I is a prodrug for the active compound wherein $R^2$, $R^3$, $R^4$ and $R^5$ are each H.

In an embodiment, $R^1$ is CH(NH$_2$)C(O)OR$^5$ and $R^2$, $R^3$, $R^4$ and $R^5$ are independently selected from H, $C_{1-18}$alkyl, $C_{1-4}$alkyleneC$_{5-6}$heterocycloalkyl and $C_{1-4}$alkylene-OC(O)$C_{1-6}$alkyl. In an embodiment $R^2$, $R^3$, $R^4$ and $R^5$ are the same.

In an embodiment, when $R^1$ is CH(NH$_2$)C(O)OR$^5$, the compound of Formula I has the following relative stereochemistry:

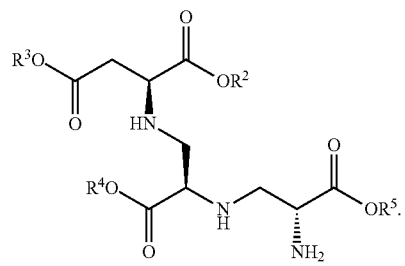

In an embodiment, $R^1$ is C(O)OR$^5$ and $R^2$, $R^3$, $R^4$ and $R^5$ are independently selected from II, $C_{1-18}$alkyl, $C_{1-4}$alkyleneC$_{5-6}$heterocycloalkyl and $C_{1-4}$alkylene-OC(O)$C_{1-6}$alkyl. In an embodiment $R^2$, $R^3$, $R^4$ and $R^5$ are the same.

In an embodiment, $R^1$ is C(O)NHR$^5$ and $R^2$, $R^3$, $R^4$ and $R^5$ are independently selected from H, $C_{1-18}$alkyl, $C_{1-4}$alkyleneC$_{5-6}$heterocycloalkyl and $C_{1-4}$alkylene-OC(O)$C_{1-6}$alkyl. In an embodiment $R^2$, $R^3$, $R^4$ and $R^5$ are the same.

In an embodiment heterocycloalkyl is

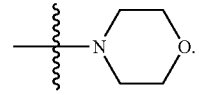

In an embodiment, n, m and p are each 1.

In an embodiment, the compound of Formula I is selected from AM-A, AM-B and lycomarasmine, or a pharmaceutically acceptable salt and/or solvate thereof. In a further embodiment, the compound of Formula I is a prodrug of AM-A, AM-B or lycomarasmine, or a pharmaceutically acceptable salt and/or solvate thereof.

The compounds of Formula I are either available via isolation from fungal sources using known natural product isolation methods or are prepared by chemical synthesis using methods known in the art. For example, compounds of Formula I wherein $R^2$, $R^3$, $R^4$ and/or $R^5$ are other than H, are available from compounds of Formula I wherein $R^2$, $R^3$, $R^4$ and/or $R^5$ are H using standard esterification or amidation methods.

The antibiotic is administered to a subject, or used, in a variety of forms depending on the selected route of administration, as will be understood by those skilled in the art. In an embodiment, the antibiotic is administered to the subject, or used, by oral (including sublingual and buccal) or parenteral (including, intravenous, intraperitoneal, subcutaneous, intramuscular, transepithelial, nasal, intrapulmonary, intrathecal, rectal, topical, patch, pump and transdermal) administration and the antibiotic formulated accordingly. Conventional procedures and ingredients for the selection and preparation of suitable compositions are described, for example, in Remington's Pharmaceutical Sciences (2000-20th edition) and in The United States Pharmacopeia: The National Formulary (USP 24 NF19) published in 1999. In general, the antibiotic is used in the form in which is it available and administered to subjects. Such forms, include, for example in the form of their pharmaceutically acceptable salts, in the form of fine particles of the zwitterionic form and in an injectable or infusable suspensions.

The compound of Formula I, or a pharmaceutically acceptable salt and/or solvate thereof, is also administered to a subject, or used, in a variety of forms depending on the selected route of administration, as will be understood by those skilled in the art. In an embodiment, the compound of Formula I is administered to the subject, or used, by oral (including sublingual and buccal) or parenteral (including, intravenous, intraperitoneal, subcutaneous, intramuscular, transepithelial, nasal, intrapulmonary, intrathecal, rectal, topical, patch, pump and transdermal) administration and the compound, salt and/or solvate, formulated accordingly. Again, conventional procedures and ingredients for the selection and preparation of suitable compositions are described, for example, in Remington's Pharmaceutical Sciences (2000—20th edition) and in The United States Pharmacopeia: The National Formulary (USP 24 NF19) published in 1999.

The pharmaceutical forms suitable for injectable use include sterile aqueous solutions or dispersions and sterile powders for the extemporaneous preparation of sterile injectable solutions or dispersions. In all cases, the form is sterile and fluid to the extent that easy syringability exists.

In an embodiment, parenteral administration is by continuous infusion over a selected period of time. Solutions suitable for parenteral administration are prepared by known methods by a person skilled in the art. For example, the antibiotic or compound of Formula I, or a salt and/or solvate thereof, is prepared in water optionally mixed with a surfactant such as hydroxypropylcellulose. Dispersions are also prepared in glycerol, liquid polyethylene glycols, DMSO and mixtures thereof with or without alcohol, and in oils. Under ordinary conditions of storage and use, these preparations contain a preservative to prevent the growth of microorganisms.

Compositions for nasal administration are conveniently formulated as aerosols, drops, gels or powders. Aerosol formulations typically comprise a solution or fine suspension of the active substance in a physiologically acceptable aqueous or non-aqueous solvent and are usually presented in single or multidose quantities in sterile form in a sealed container, which take the form of a cartridge or refill for use with an atomising device. Alternatively, the sealed container is a unitary dispensing device such as a single dose nasal inhaler or an aerosol dispenser fitted with a metering valve which is intended for disposal after use. Where the dosage form comprises an aerosol dispenser, it contains a propellant which is, for example, a compressed gas such as compressed air or an organic propellant such as fluorochlorohydrocarbon. In an embodiment, the aerosol dosage forms take the form of a pump-atomizer.

Compositions suitable for buccal or sublingual administration include tablets, lozenges, and pastilles, wherein the active ingredient is formulated with a carrier such as sugar, acacia, tragacanth, gelatin and/or glycerine. Compositions for rectal administration are conveniently in the form of suppositories containing a conventional suppository base such as cocoa butter.

In another embodiment, the antibiotic or compound of Formula I, or a salt and/or solvate thereof, is orally administered, for example, with an inert diluent or with an assimilable edible carrier, or it is enclosed in hard or soft shell gelatin capsules, or it is compressed into tablets, or it is incorporated directly with the food of a diet. For oral administration, the antibiotic or compound of Formula I, or a salt and/or solvate thereof, is incorporated with excipients and used in the form of, for example, ingestible tablets, buccal tablets, troches, capsules, elixirs, suspensions, syrups, wafers, and the like. Oral dosage forms also include modified release, for example immediate release and timed-release, formulations. Examples of modified-release formulations include, for example, sustained-release (SR), extended-release (ER, XR, or XL), time-release or timed-release, controlled-release (CR), or continuous-release (CR or Contin), employed, for example, in the form of a coated tablet, an osmotic delivery device, a coated capsule, a microencapsulated microsphere, an agglomerated particle, e.g., molecular sieving type particles, or, a fine hollow permeable fiber bundle, or chopped hollow permeable fibers, agglomerated or held in a fibrous packet. In an embodiment, timed-release compositions are, formulated, as liposomes or those wherein the active compound is protected with differentially degradable coatings, such as by microencapsulation, multiple coatings, etc. Liposome delivery systems include, for example, small unilamellar vesicles, large unilamellar vesicles and multilamellar vesicles. In an embodiment, liposomes are formed from a variety of lipids, such as cholesterol, stearylamine or phosphatidylcholines.

It is also possible to freeze-dry the antibiotic or compound of Formula I, or a salt and/or solvate thereof, and use the lyophilizate obtained, for example, for the preparation of products for injection.

In an embodiment, the antibiotic or compound of Formula I, or a salt and/or solvate thereof, is coupled with soluble polymers as targetable drug carriers. Such polymers include, for example, polyvinylpyrrolidone, pyran copolymer, polyhydroxypropylmethacrylamide-phenol, polyhydroxy-ethyl-aspartamide-phenol, or polyethyleneoxide-polylysine substituted with palmitoyl residues. In a further embodiment, the antibiotic or compound of Formula I, or a salt and/or solvate thereof, is coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

The antibiotic and the compound of Formula I, or a salt and/or solvate thereof, are used in combination with each other. The antibiotic and the compound of Formula I, or a salt and/or solvate thereof, are either used or administered separately in time and/or in mode of administration (i.e. different administration routes) or they are administered together in the same pharmaceutical preparation.

In one embodiment the antibiotic and the compound of Formula I, or a salt and/or solvate thereof, are used or administered separately in time and/or in mode of administration. For example, the antibiotic is administered by injection and the compound of Formula I, or a salt and/or solvate thereof, is administered orally. In another example, the antibiotic is administered orally and the compound of Formula I, or a salt and/or solvate thereof, is administered by injection. In a further example, both the antibiotic and the compound of Formula I, or a salt and/or solvate thereof, are administered by injection. When the antibiotic and the compound of Formula I, or a salt and/or solvate thereof, are used or administered separately in time and/or in mode of administration, the antibiotic is administered, or used, either before or after administration, or use, of the compound of Formula I, or a salt and/or solvate thereof.

In another embodiment, the antibiotic and the compound of Formula I, or a salt and/or solvate thereof, are administered contemporaneously. As used herein, "contemporaneous administration" of two substances to a subject means providing the antibiotic and the compound of Formula I, or a salt and/or solvate thereof, so that they are both biologically active in the subject at the same time. The exact details of the administration will depend on the pharmacokinetics of the antibiotic and the compound of Formula I, or a salt and/or solvate thereof, in the presence of each other, and can include administering antibiotic and the compound of Formula I, or a salt and/or solvate thereof, within a few hours of each other, or even administering the antibiotic and the compound of Formula I, or a salt and/or solvate thereof, within 24 hours or greater of administration of the other, if the pharmacokinetics are suitable. Design of suitable dosing regimens is routine for one skilled in the art.

In an embodiment, the antibiotic and the compound of Formula I, or a salt and/or solvate thereof, are administered to a subject in a single composition or formulation.

In another embodiment of the present application, the antibiotic and the compound of Formula I, or a salt and/or solvate thereof, are administered to a subject in a non-contemporaneous fashion.

In a further embodiment of the present application, the antibiotic and the compound of Formula I, or a salt and/or solvate thereof, are administered to the subject in a contemporaneous fashion followed by, or alternating with, administration in a non-contemporaneous fashion.

Treatment methods comprise administering to a subject the antibiotic and the compound of Formula I, or a salt and/or solvate thereof, and optionally consists of a single administration, or alternatively comprises a series of administrations. The length of the treatment period depends on a variety of factors, such as the severity of the disease, disorder or condition, the age of the subject, the dosage of the antibiotic and the compound of Formula I, or a salt and/or solvate thereof, the activity of the antibiotic and the compound of Formula I, or a salt and/or solvate thereof, and/or a combination thereof.

It is an embodiment that that antibiotic is administered or used according to treatment protocol that is known for the antibiotic in the treatment in bacterial infections.

In an embodiment, the antibiotic and the compound of Formula I, or a salt and/or solvate thereof, are administered or used as soon as possible after exposure to the bacteria. In an embodiment, the antibiotic and the compound of Formula I, or a salt and/or solvate thereof, are administered or used until treatment of the bacterial infection is achieved. For example, until complete elimination of the bacteria is achieved, or until the number of bacteria has been reduced to the point where the subject's defenses are no longer overwhelmed and can kill any remaining bacteria.

The dosage of the antibiotic and the compound of Formula I, or a salt and/or solvate thereof, varies depending on many factors such as the pharmacodynamic properties thereof, the mode of administration, the age, health and weight of the subject, the nature and extent of the symptoms, the frequency of the treatment and the type of concurrent treatment, if any, and the clearance rate in the subject to be treated. One of skill in the art can determine the appropriate dosage based on the above factors. The antibiotic and the compound of Formula I, or a salt and/or solvate thereof, may be administered initially in a suitable dosage that may be adjusted as required, depending on the clinical response.

In an embodiment, the dosage of the antibiotic is equal to or less than the dosage of such agents when used alone. Such dosages are known to or readily determined by those skilled in the art.

III. Compositions and Kits of the Application

The present application also includes a pharmaceutical composition comprising:
one or more β-lactam antibiotics; and
one or more compounds of Formula I:

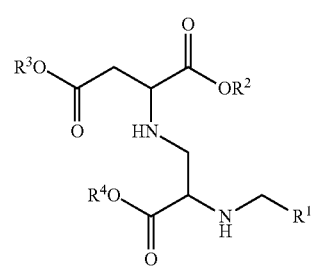

wherein
$R^1$ is selected from $C(O)OR^5$, $C(O)NHR^5$ and $CH(NH_2)C(O)OR^5$;
$R^2$, $R^3$, $R^4$ and $R^5$ are independently selected from H, $C_{1-24}$alkyl, $C_{1-6}$alkylene$C_{6-10}$aryl, $C_{1-6}$alkylene$C_{3-10}$cycloalkyl, $C_{1-6}$alkylene$C_{3-10}$heterocycloalkyl and $C_{1-6}$alkylene-$OC(O)C_{1-6}$alkyl; and
n, m and p are independently selected from 1 and 2;
or a pharmaceutically acceptable salt and/or solvate thereof, and
the one or more β-lactam antibiotics and one or more compounds of Formula I are present in amounts that are effective to treat a bacterial infection, or a disease, disorder or condition arising from a bacterial infection.

The present application also includes a pharmaceutical composition comprising:
one or more β-lactam antibiotics; and
one or more compounds of Formula I as defined above, or a pharmaceutically acceptable salt and/or solvate thereof, and
the one or more β-lactam antibiotics and one or more compounds of Formula I are present in amounts that are effective for improving the efficacy of the β-lactam antibiotic for the treatment of a bacterial infection or a disease, disorder or condition arising from a bacterial infection.

The present application also includes a kit for the treatment of a bacterial infection or a disease, disorder or condition arising from a bacterial infection, the kit comprising:
one or more β-lactam antibiotics;
one or more compounds of Formula I:

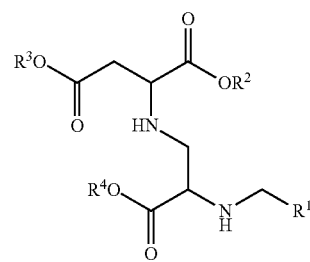

wherein
$R^1$ is selected from $C(O)OR^5$, $C(O)NHR^5$ and $CH(NH_2)C(O)OR^5$;
$R^2$, $R^3$, $R^4$ and $R^5$ are independently selected from H, $C_{1-24}$alkyl, $C_{1-6}$alkylene$C_{6-10}$aryl, $C_{1-6}$alkylene$C_{3-10}$cycloalkyl, $C_{1-6}$alkylene$C_{3-10}$ heterocycloalkyl and $C_{1-6}$alkylene-$OC(O)C_{1-6}$alkyl; and n, m and p are independently selected from 1 and 2;
or a pharmaceutically acceptable salt and/or solvate thereof; and optionally instructions for administration of the one or more β-lactam antibiotics and the one or more compounds of Formula I, or a pharmaceutically acceptable salt and/or solvate thereof, to a subject in need thereof.

The present application also includes a kit for the treatment of a bacterial infection, or a disease, disorder or condition arising from a bacterial infection, the kit comprising:
one or more compounds of Formula I as defined above, or a pharmaceutically acceptable salt and/or solvate thereof; and
instructions for administration of the one or more compounds of Formula I, or a pharmaceutically acceptable salt and/or solvate thereof, to a subject being administered an antibiotic for a bacterial infection or a disease, disorder or condition arising from a bacterial infection.

The present application also includes a kit for improving the efficacy of a β-lactam antibiotic for the treatment of a bacterial infection or a disease, disorder or condition arising from a bacterial infection, the kit comprising:
one or more β-lactam antibiotics;
one or more compounds of Formula I as defined above, or a pharmaceutically acceptable salt and/or solvate thereof; and
optionally instructions for administration of the one or more β-lactam antibiotics and the one or more compounds of Formula I, or a pharmaceutically acceptable salt and/or solvate thereof, to a subject in need thereof.

The present application also includes a kit for improving the efficacy of an β-lactam antibiotic for the treatment of a bacterial infection, or a disease, disorder or condition arising from a bacterial infection, the kit comprising:
one or more compounds of Formula I as defined above, or a pharmaceutically acceptable salt and/or solvate thereof; and
instructions for administration of the one or more compounds of Formula I as defined above, or a pharmaceutically acceptable salt and/or solvate thereof, to a subject being administered the β-lactam antibiotic for the treatment of a bacterial infection or a disease, disorder or condition arising from a bacterial infection.

The one or more antibiotics are selected from any antibiotic which treats metallo-β-lactamase-expressing bacterial infections. In an embodiment, the one or more antibiotics are β-lactam antibiotics. In an embodiment, the β-lactam antibiotic is selected from penicillin derivatives (penems), cephalosporins (cephems), monobactams and carbapenems. In an embodiment, the β-lactam antibiotic is selected from imipenem, ertapenem, meropenem, doripenem, biapenem, panipenem, ticarcillin, ampicillin, amoxicillin, carbenicillin, piperacillin, azlocillin, mezlocillin, ticarcillin, cefoperazone, cefotaxime, ceftriaxone and ceftazidime.

In another embodiment, the one or more antibiotics are carbapenem antibiotics. In an embodiment, the carbapenem antibiotic is selected from meropenem, biapenem, doripenem, panipenem and imipenem.

In an embodiment, the compound of Formula I has the following relative stereochemistry:

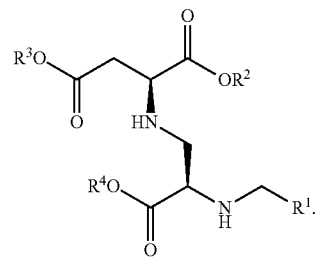

In an embodiment, $R^2$, $R^3$, $R^4$ and $R^5$ are each, H. In an embodiment, and $R^2$, $R^3$, $R^4$ and $R^5$ are independently selected from $C_{1-18}$alkyl, $C_{1-4}$alkylene$C_{5-6}$heterocycloalkyl and $C_{1-4}$alkylene-OC(O)$C_{1-6}$alkyl. In an embodiment, $R^2$, $R^3$, $R^4$ and $R^5$ are the same and are selected from $C_{1-18}$alkyl, $C_{1-4}$alkylene$C_{5-6}$heterocycloalkyl and $C_{1-4}$alkylene-OC(O)$C_{1-6}$alkyl.

In an embodiment, when at least one of $R^2$, $R^3$, $R^4$ and $R^5$ is other than H, the compound of Formula I is a prodrug for the active compound wherein $R^2$, $R^3$, $R^4$ and $R^5$ are each H.

In an embodiment, $R^1$ is $CH(NH_2)C(O)OR^5$ and $R^2$, $R^3$, $R^4$ and $R^5$ are independently selected from H, $C_{1-18}$alkyl, $C_{1-4}$alkylene$C_{5-6}$heterocycloalkyl and $C_{1-4}$alkylene-OC(O)$C_{1-6}$alkyl. In an embodiment $R^2$, $R^3$, $R^4$ and $R^5$ are the same. In an embodiment, when $R^1$ is $CH(NH_2)C(O)OR^5$, the compound of Formula I has the following relative stereochemistry:

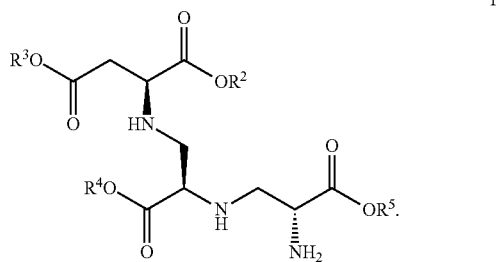

In an embodiment, $R^1$ is $C(O)OR^5$ and $R^2$, $R^3$, $R^4$ and $R^5$ are independently selected from H, $C_{1-18}$alkyl, $C_{1-4}$alkylene$C_{5-6}$heterocycloalkyl and $C_{1-4}$alkylene-OC(O)$C_{1-6}$alkyl. In an embodiment $R^2$, $R^3$, $R^4$ and $R^5$ are the same.

In an embodiment, $R^1$ is $C(O)NHR^5$ and $R^2$, $R^3$, $R^4$ and $R^5$ are independently selected from H, $C_{1-18}$alkyl, $C_{1-4}$alkylene$C_{5-6}$heterocycloalkyl and $C_{1-4}$alkylene-OC(O)$C_{1-6}$alkyl. In an embodiment $R^2$, $R^3$, $R^4$ and $R^5$ are the same.

In an embodiment heterocycloalkyl is

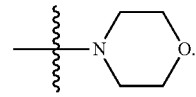

In an embodiment, n, m and p are each 1.

In an embodiment, the compound of Formula I is selected from AM-A, AM-B and lycomarasmine, or a pharmaceutically acceptable salt and/or solvate thereof. In a further embodiment, the compound of Formula I is a prodrug of AM-A, AM-B or lycomarasmine, or a pharmaceutically acceptable salt and/or solvate thereof.

In an embodiment, the one or more compounds of Formula I as defined above, or a pharmaceutically acceptable salt and/or solvate thereof, and the one or more β-lactam antibiotics in the compositions and kits of the present application are formulated as separate pharmaceutical compositions, for separate administration to, or use in, subjects. In this embodiment, the separate pharmaceutical compositions are formulated independently of each other and in accordance with the desired mode of administration for each active. In an embodiment, the one or more β-lactam antibiotics are formulated for administration, or use, by oral delivery or for delivery by injection. In another embodiment, the one or more compounds of Formula I as defined above, or a pharmaceutically acceptable salt and/or solvate thereof are formulated for administration, or use, by oral delivery or for delivery by injection.

In an embodiment, the one or more compounds of Formula I as defined above, or a pharmaceutically acceptable salt and/or solvate thereof, and the one or more β-lactam antibiotics in the compositions and kits of the present application are formulated as a single pharmaceutical composition, for combined, simultaneous administration to, or use in, subjects. In an embodiment, the single pharmaceutical composition is formulated for administration, or use, by oral delivery or by injection.

IV. Cell-Based Antibiotic Resistance Assay

The present application also includes a cell-based screening assay comprising bacterial cells that express a bacterial resistance gene, wherein the cells are modified to be deficient in one or more of (i) genes encoding proteins that block the entry of molecules into the cells and (ii) genes encoding proteins that facilitate efflux of molecules out of the cells.

In an embodiment, the bacterial cells are $E.\ coli$ cells. In a further embodiment, the gene encoding a protein that blocks the entry of molecules into the cells is bamB. In another embodiment, the gene encoding a proteins that facilitates efflux of molecules out of the cells tolC. In a further embodiment, the bacterial resistance gene is a gene encoding a metallo-β-lactamase, such as the $bla_{NDM-1}$ gene.

In an embodiment, the present application also includes a method of identifying compounds that treat antibiotic resistance comprising:

(a) contacting one or more compounds with bacterial cells that express a bacterial resistance gene, wherein the cells are modified to be deficient in one or more of (i) genes encoding proteins that block the entry of molecules into the cells and (ii) genes encoding proteins that facilitate efflux of molecules out of the cells, and wherein the one or more compounds are contacted with the cells in the presence of an antibiotic that is susceptible to a protein encoded by the bacterial resistance gene; and (b) identifying compounds that inhibit growth of the bacterial cells as compounds that treat antibiotic resistance.

In embodiment, the inhibition of growth of the bacterial cells by the compounds is compared with controls.

Antibiotics that are susceptible to a protein encoded by the bacterial resistance gene are antibiotics whose efficacy is reduced in the presence of a protein encoded by the resistance gene.

The following non-limiting examples are illustrative of the present application:

EXAMPLES

Example 1: Isolation and Activity of AM-A

Materials and Methods (a) Reagents.

All enzymes and chemicals of analytical grade were purchased from Sigma-Aldrich, unless otherwise stated. Proton and carbon NMR spectra were recorded on a Bruker 700 MHz spectrometer. Nitrocefin was synthesized as reported previously[21].

(b) DNA Manipulations and Plasmid Construction.

Plasmid DNA purification and gel extraction were performed using the PureLink™ Quick plasmid miniprep and PureLink™ Quick gel extraction kits (Invitrogen), respectively. Restriction enzymes were purchased from Fermentas. Primers for PCR DNA amplification were purchased from IDT (Coralville, Iowa). PCR was performed using Phusion High-Fidelity DNA polymerase (Thermo Scientific) using reaction conditions specified by the manufacturer. All ligation reactions were performed using T4 DNA ligase (Thermo Scientific) according to manufacturer's instructions. All β-lactamase overexpression constructs were generated without the leader peptide in a pET-28b plasmid containing a N-terminal His Tag. Leader peptide sequences were determined using SignalP 4.0 25 All vectors were transformed in $E.\ coli$ TOP10 chemically competent cells.

(c) Protein Purification.

VIM-2, IMP-7, CTX-M-15, TEM-1, and OXA-48: An $E.\ coli$ BL21(DE3) colony transformed with its respective β-lactamase construct was inoculated into LB medium containing 50 μg/mL kanamycin and grown at 37° C. Protein expression was induced with 1 mM IPTG at OD600 0.7 and cultures were incubated overnight at 16° C. Cells were harvested by centrifugation and cell paste from 1 L of culture expressing P3-lactamase was washed with 8 mL 0.85% NaCl, resuspended in buffer containing 20 mM HEPES pH 7.5, 500 mM NaCl, 20 mM imidazole and 20 M ZnSO4 (for metalloenzymes) then lysed by sonication. Lysate was centrifuged using a Beckman JA 25.50 rotor at 20 000 RPM (48 254×g) for 45 min at 4° C. The supernatant was applied to a 5-mL HiTrap Ni-NTA column (GE Lifesciences) at a constant flow rate of 3 mL/min. The column was washed with 5 column volumes of the same buffer and step gradients of increasing imidazole were used for wash and elution steps. Fractions containing purified β-lactamase, based on SDS-PAGE, were pooled and dialyzed overnight at 4° C. in buffer containing 20 mM HEPES pH 7.5, 150 mM NaCl, 20% glycerol and 20 μM ZnSO4 for metalloenzymes. NDM-1 was purified as above with the addition of 84 μg SUMO protease. Protease and uncleaved NDM-1 were removed by applying dialyzed solution to a 5-mL HiTrap Ni-NTA column and collecting the flow through fractions. All purified enzymes were verified to be >95% pure as assessed by SDS-PAGE and stored at −20° C.

(d) Cell-Based Screen.

~500 natural product extracts were screened against $E.\ coli$ BW25113ΔbamBΔto1CΔaraDAB::pLac(blaNDM-1) in combination with 0.125 μg/mL meropenem. The screen was conducted in 96-well plates in duplicate using cation-adjusted Mueller-Hinton broth (CAMHB). Low growth control was 2×MIC meropenem (1 μg/mL) and growth control was ¼ MIC meropenem (0.125 μg/mL). Z' was determined to be 0.77, indicating an excellent screening window[22].

(e) Purification of AM-A.

WAC-138 (*Aspergillus versicolor*) (4 L) was evaporated under reduced pressure with 2% (W/V) HP-20 resin (Diaion) to give a residue, WAC138-E. The crude mixture was applied on a HP-20 (100 g) column eluting with $H_2O$ (1 L), 10% MeOH (1 L), 25% MeOH (1 L), 60% MeOH (1 L), and 100% MeOH (1 L) to yield five fractions, WAC138-E-1~5. The active fraction WAC138-E-1 was applied to reverse-phase CombiFlash ISCO (RediSep Rf C18, Teledyne) and eluted with a Water-Acetonitrile linear gradient system (0-100% Acetonitrile) to give 65 fractions WAC138-E-1-1~65. The active subfractions WAC138-E-1-5 were passed through a Sephadex LH-20 column (100 ml), eluting with 25% MeOH, to yield 12 subfractions. The active subfractions WAC138-E-1-5-6~8 were combined and recrystallized in 5 ml 1% acetic acid (V/V) to give AM-A as white crystals. 1 L of culture yielded ~200 mg AM-A. $\alpha_D^{20}$=−48.9° (previously reported value=−48°)[23]. Predicted mass=308.1094 m/z. Exact mass=308.1094 m/z. Optical rotations were determined on a Perkin-Elmer 241 polarimeter. Mass was determined using a Bruker Maxis 4 G Q/TOF, ESI MS Direct infusion (3 μL/min) in positive ion mode.

(f) $IC_{50}$ Enzyme Inhibition Assays.

Enzyme (NDM-1, 5 nM; VIM-2, 500 pM; CTX-M-15, 500 pM; KPC-2, 5 nM; OXA-48, 1 nM; TEM-1, 100 pM; ACE, 50 nM) was mixed with 30 μM nitrocefin (100 μM nitrocefin for TEM-1; 250 M furanacryloyl-L-phenylalanyl-glycylglycine [FAPGG] for ACE[24]) after a 5-10 minute preincubation with AM-A. Metallo-enzymes were supplemented with 10 μM $ZnSO_4$. Assays were read in 96-well microplate format at 490 nm using a Spectramax reader (Molecular Devices) at 30-37° C.

(g) Incubation of AM-A with Metalloenzymes.

Enzyme (500 nM) was incubated with AM-A (500 μM) for 10 minutes. 20 μL of the above was diluted with 180 μL nitrocefin or FAPGG substrate for the following final concentrations: Enzyme (50 nM), FAPGG (50 μM)/nitrocefin (20 μM), AM-A (50 μM). Buffer (50 mM HEPES pH 7.5, 300 mM NaCl) was stirred overnight with 2 g/100 mL Chelex-100 (Biorad; Richmond, Calif.). Assays were read in 96-well microplate format at 490 nm using a Spectramax reader (Molecular Devices) at 37° C.

(h) Reversibility Assays.

5 mL NDM-1 (500 nM) was incubated either with AM-A (100 μM), or without, on ice for 1 hour. The no enzyme control was buffer alone (Chelex-treated 50 mM HEPES pH 7.5). 2.5 mL was passed through a PD-10 spin column (GE healthcare) following column equilibration with buffer and centrifuged at 2,000×g for 2 minutes. Pre-PD-10 (+AM-A, −AM-A, −NDM-1), Post-PD-10 ((+AM-A, −AM-A, −NDM-1), and nitrocefin were equilibrated to 30° C. 20 μL of the enzyme solution was added to 180 μL nitrocefin for final enzyme concentration of 50 nM, and nitrocefin of 100 μM and AM-A of 10 μM. Assays were read in 96-well microplate format at 490 nm using a Spectramax reader (Molecular Devices) for 1 hr at 30° C.

(i) $Zn^{2+}$ Restoration Assays.

NDM-1 (5 nM) supplemented with 10 pM $ZnSO_4$ was incubated with 20 μM AM-A for 15 minutes at 30° C. Nitrocefin (30 μM) and $ZnSO_4$ from 500 nM-40 μM were added to a final volume of 100 μL and absorbance at 490 nm was monitored using a Spectramax reader (Molecular Devices) for 30 minutes at 30° C. Percent residual activity was calculated from no AM-A control. Slightly negative percent residual activity was reported as 0.

(j) Inactivation Kinetics.

NDM-1 (50 nM) was added to 20 μM nitrocefin containing AM-A in serial ½ dilutions from 8 μM. The assay was performed in 50 mM HEPES pH 7.5, 200 μL final volume. The assay was read in 96-well microplate format at 490 nm using a Spectramax reader (Molecular Devices) for 10 minutes at 37° C. VIM-2 (10 nM) was added to 20 μM nitrocefin containing AM-A in serial ½ dilutions from 16 μM. The assay was performed in 50 mM HEPES pH 7.5, 200 μL final volume. The assay was read in 96-well microplate format at 490 nm using a Spectramax reader (Molecular Devices) for 10 minutes at 37° C. as reported previously. For all assays experiments the offset between reaction initiation and the first read was ~6s.

Rate constants characterizing the inactivation of enzyme were calculated based on the dependence of the pseudo-first order rate constant, ki, upon AM-A concentration according to the following model:

where E•Zn, A, E•Zn•A, and Zn•A are the active metalloenzyme, AM-A, the ternary metalloenzyme-AM-A complex, and AM-A-metal complex, respectively. $K_i$ represents the dissociation constant of the ternary complex and $k_{+2}$ is the rate constant for dissociation of ternary complex into inactivated enzyme ($E_{inact}$) and AM-A-Zn complex. Steady-state progress curves were fit to the integrated equation:

$$P = \frac{v_0}{k_i}(1 - e^{-k_i i}) \qquad (1)$$

Where $v_0$ is the initial rate of reporter substrate turnover and $k_i$ is the pseudo-first-order inactivation rate constant. The individual values of $K_i$ and $k_{+2}$ were determined by fitting the value of $k_i$ to equation 2 as described previously[25]:

$$k_i = \frac{k_{+2} \cdot [A]}{K_i(1 + [S]/K_M) + [A]} \qquad (2)$$

where [A] is the concentration of AM-A and [S] and $K_M$ were the concentration and $K_M$ of the reporter substrate, respectively.

(k) ICP Mass Spectrometry.

Inductively coupled mass spectrometry (ICP-MS) was used to analyze the ability of AM-A to chelate $Zn^{66}$ from purified NDM-1 (27-270). The NDM-1 protein was purified as previously described[26] and freshly exchanged using a 15 kDa cutoff dialysis tubing into ICP-MS buffer (20 mM HEPES, 100 mM NaCl, pH 7.5) overnight at 4° C. in order to remove any contaminating metals. The protein was concentrated to ~5 mg/mL and varying concentrations of AM-A were incubated with the protein samples in triplicate for 3 hours at room temperature with gentle shaking. The protein-AM-A samples were again dialyzed overnight at 4° C. into ICP-MS buffer using 12-14 kDa cutoff D-tube dialyzer mini (EMD biosciences) microdialysis cassettes. The final protein was diluted to 1 mg/mL in ICP-MS buffer, followed by a ¹⁄₄₀ dilution in an internal standard (10 ug/L Sc45, 1% nitric acid, Inorganic Ventures). Prior to sample analysis, the ICP MS was calibrated using a standard solution containing the metal isotopes of interest (Inorganic Ventures). The protein sample was then transferred by nebulization into a NexION 3000 ICP mass spectrometer (Perkin Elmer). Quantitative analysis was performed in triplicate for each sample with 60 sweeps per reading using the peak-hopping mode with a 50 ms/AMU dwell time for each element. Instrument settings were: rf power (1600 W), integration time (35s), collision gas (Ar40), RPQ voltage (25V) and sample flow rate (4 rpm). Isotope abundance was determined by integrating peak areas using the NexION software program, and the data was represented graphically using Microsoft Excel.

(l) FIC Index Determination.

FIC values were determined by standard methods[27] setting up checkerboards with 8 concentrations of each meropenem and AM-A in serial ½ dilutions. Experiments were done in duplicate and the mean used for calculation. The MIC for each compound was the lowest concentration of compound showing no growth. The FIC for each compound was calculated as the concentration of the compound in the presence of co-compound for a well showing no growth, divided by the MIC for that compound. The FIC index is the sum of the two FICs.

(m) Clinical Isolate Screening

Various concentrations of AM-A were chosen in combination with 2 mg/L of meropenem which is the EUCAST breakpoint for resistance[28]. Synergistic properties of the two compounds were examined in a micro-titre tray using BHI as the growth medium (Oxford Science Park, England) and an inoculum of 0.5 MacFarland. All plates contained the control strains *Escherichia coli* ATCC 25922 and *Pseudomonas aeruginosa* ATCC 27853. Overall, 226 non-clonal clinical isolates (Enterobacteriaceae, *P. aeruginosa* and *Acinetobacter* spp.) were challenged containing one of the following MBLs: SPM-1 (n=17), AIM-1 (n=8), NDM-1 (n=67), VIM-type (n=114) or IMP-type (n=20). Three *E. coli* and 5 *K. pneumoniae* carrying VIM-1 also carried the serine carbapenemase KPC; and 4 *E. coli* and one *K. pneumoniae* carrying NDM-1 also possessed the carbapenemase OXA-181. Plates were incubated at 37° C. and read after 18 hrs. A sub-set of strains (#48) were repeated to examine reproducibility and showed no deviation from the original data.

(n) Animal Studies.

All animals were housed in specific pathogen-free units in the Central Animal Facility at McMaster University. All experimental protocols were approved by, and performed in accordance with the McMaster Animal Research Ethics Board. Female CD1 mice were purchased from Charles River.

(o) Bacterial Infections.

Mice were infected intraperitoneally (ip) with a dose of 2×106 colony forming units (cfu) of *Klebsiella pneumoniae* N11-2218 for all organ bacterial load experiments, or with a dose of 5×107cfu for all survival experiments. For all organ bacterial load experiments, mice were euthanized 48 hours post infection, and spleen and liver were harvested. Organs were placed into 1 mL sterile PBS on ice, and then homogenized (Mixer Mill 400; Retsch). Organ homogenates were then serially diluted in PBS, and plated on Brilliant Green agar (Oxoid) for cfu enumeration. For survival curves, mice were monitored for endpoint. For all experiments, mice were treated 30 minutes post infection with a specified subcutaneous dose of either PBS, meropenem, AM-A inhibitor, or a combination of both antibiotic and inhibitor.

Results and Discussion

*E. coli* strain BW25113 was modified by deletion of the bamB and tolC genes so as to increase permeability to and reduce efflux of small molecules. This strain was then further modified by the single-copy chromosomal insertion of the bla$_{NDM-1}$ gene under control of the pLac promoter. Microbial natural product extracts were screened against this strain in the presence of sublethal ¼ MIC meropenem. AM-A was purified from a hit extract and its structure elucidated by NMR, mass spectrometry and polarimetry. IC$_{50}$ values for AM-A were determined using nitrocefin (for MBLs and Ser BLs) and furanacryloyl-L-phenylalanylglycylglycine (for ACE)[21] as reporter substrates against the following purified enzymes: MBLs IMP-7, VIM-2, and NDM-1; SBLs CTX-M-15, KPC-2, OXA-48, and TEM-1; as well as ACE from rabbit lung. IC$_{50}$, reversibility, Zn$^{2+}$ restoration, and inactivation enzyme assays were performed in 50 mM HEPES pH 7.5 and measured using a SpectraMax reader (Molecular Devices). ICP-MS experiments were conducted using purified NDM-1 at 5 mg/mL and varying concentrations of AM-A with subsequent dilution and transfer by nebulization into a NexION 3000 ICP mass spectrometer (Perkin Elmer). FIC values were determined using standard methods[27]. Various concentrations of AM-A were tested in combination with 2 mg/L meropenem against 200+MBL-expressing clinical isolates including *Pseudomonas* spp., *Acinetobacter* spp., and Enterobacteriaceae. A dose of 2×10$^6$ forming units (cfu) of *Klebsiella pneumoniae* N11-2218 was used for all organ bacterial load experiments and a dose of 5×10$^7$cfu for all survival experiments. For all experiments, mice were treated with compound 30 minutes post infection.

AM-A showed potent in vitro dose-dependent inhibition of NDM-1 and the related MBL VIM-2 (FIG. 1*b*), with weaker activity against the IMP-7 MBL. AM-A had no effect on the Serine β-lactamases TEM-1 and CTX-M-15 as well as the Serine-carbapenemases KPC-2 and OXA-48 (FIG. 1*b*). Inhibition of NDM-1 was shown to be irreversible after removal of AM-A by gel filtration (FIG. 1*c*), but enzymatic activity could be restored by addition of excess ZnSO$_4$ consistent with a metal depletion mechanism (FIG. 1*d*). The inhibition of mammalian metalloenyzmes could be seen as a potential side effect however AM-A was only able to reduce the activity of rabbit lung ACE by ~35% in concentration-response assays. Extended incubation of the metalloenzymes NDM-1, VIM-2, IMP-7, and ACE at high concentrations of AM-A (0.5 mM) in Zn$^{2+}$-depleted buffer prepared as previously described[29] led to complete inactivation of NDM-1 and VIM-2, and ~70% and ~50% inhibition of activity in IMP-7 and ACE, respectively demonstrating selectivity toward NDM and VIM MBLs. Time-dependent inactivation was shown to be saturable for NDM-1 (K$_i$=11 nM, k$_{+2}$=0.0062 s$^{-1}$) and VIM-2 (K$_i$=7 nM, k$_{+2}$=0.0065 s$^{-1}$) (FIG. 1*e*), consistent with an inactivation mechanism whereby AM-A removes Zn$^{2+}$. This mechanism of action was confirmed by inductively coupled mass spectrometry that showed a loss of ~1.8 Zn equivalents in NDM-1 inactivated by AM-A (FIG. 1*t*).

Systematic titration of AM-A and meropenem concentrations against the engineered *E. coli* and a panel of clinical CRE strains demonstrated that AM-A restored meropenem activity consistent with NDM inhibition. Checkerboard MIC studies confirmed the expected synergy between meropenem and AM-A only in NDM-1 expressing CRE and not in carbapenem sensitive strains (FIG. 2*a, b*). Fractional inhibitory concentration (FIC) index values were determined to be <0.1 for a panel of 16 clinical CRE isolates tested against meropenem and AM-A combinations (FIC values of ≤0.5 are defined as synergistic[27]). Potentiation of AM-A (8 µg/ml) with meropenem was further investigated using 229 MBL positive (SPM-1, IMP, NDM, AIM and VIM) non-clonal clinical isolates (Enterobacteriaceae, *Acinetobacter* spp. and *Pseudomonas* spp.) (FIG. 2*c*). 76 isolates were also tested that possessed serine carbapenemases, or MBLs and serine carbapenemases. Strains were amassed over a 10 year period as part of a global MBL collection including isolates from Russia, India, Pakistan, Australia, North Africa, and South America. AM-A restored meropenem sensitivity (2 μg/ml) in 88% of NDM positives isolates and 90% of VIM positive isolates. Importantly, AM-A was active in *Pseudomonas* spp. (mainly *Pseudomonas aeruginosa*), which are viewed as a highly challenging model for new antibiotics. AM-A showed very little potentiation with SPM-1, IMP and AIM but these MBLs are less numerous than the "global" VIM and NDM MBLs and therefore deemed to be less clinically relevant. The lack of potentiation with IMP-expressing strains correlates well with biochemical data showing less potent inactivation of purified IMP-7 compared to NDM-1 or VIM-2.

The resistance profile of NDM-1-positive clinical CRE and the efficacy with which AM-A potentiated meropenem activity against NDM-1-positive clinical CRE suggested that AM-A would reverse NDM-1-mediated resistance to meropenem in vivo and restore clinical efficacy of this antibiotic. To test this, CD1 mice were infected intraperitoneally with a lethal dose of NDM-1-positive *K. pneumoniae* N11-2218 to initiate a lethal systemic infection and the effects of meropenem or AM-A monotherapy or antibiotic-inhibitor combination therapy was evaluated. Preliminary dosing experiments determined empirically that the bacterial load of NDM-1-positive *K. pneumoniae* in tissues was unaffected by treatment with AM-A alone, and that this strain was resistant to meropenem monotherapy at doses below 50 mg/kg, leading to lethal infection. However, combination therapy with AM-A and meropenem significantly reduced the bacterial load in the spleen (FIG. 3a) and to a lesser extent in the liver (FIG. 3b) after a single intraperitoneal dose. Remarkably, while meropenem or AM-A alone were unable to prevent lethal infection by NDM-1-positive *K. pneumoniae*, a single dose of combination therapy led to >95% survival at 5 days following infection (FIG. 3c).

AM-A presents a non-toxic candidate for an antibiotic adjuvant that can overcome resistance mediated by NDM and VIM MBLs and re-sensitize carbapenem-resistant Gram-negative pathogens to carbapenems. Active drug/inhibitor combinations continue to be highly successful in the clinic with inhibitors targeted to Ser-β-lactamases[30]. AM-A presents for the first time, in vitro and in vivo, complementary activity against key MBLs that have become rapidly global and result in significant human morbidity particularly in developing countries. In combination with a β-lactam antibiotic such as meropenem as shown here, resistance can be overcome and antibiotic activity fully restored. AM-A, or semi-synthetic derivatives, are therefore excellent leads for an antibiotic adjuvant co-therapy to address the recent emergence of MBLs in the clinic.

Example 2: Prodrugs of AM-A

In this example, various prodrugs of AM-A are prepared.
(a) General Chemistry

Prodrugs of AM-A are prepared by activating the carboxylic acid groups in AM-A followed by addition of the appropriate nucleophile in the presence of a base. Neutralization of the reaction mixture followed by isolation provides the following prodrugs of AM-A:

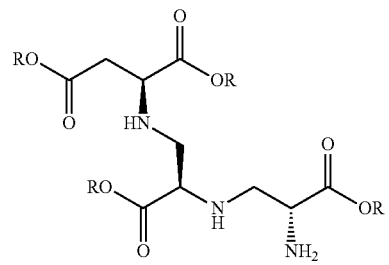

R=—CH₃, —(CH₂)ₓCH₃ (x=1, 2, 3, 4, 5, 6, 7, 8, 9, 10, 11, 12, 13, 15, 15, 16 17 or 18), —CH₂OC(O)t-Bu and

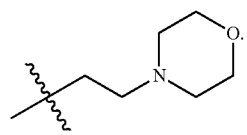 [SMILES: *CCN1CCOCC1]

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS FOR DOCUMENTS REFERRED TO IN THE SPECIFICATION

[1] Frére, J. M. *Beta-Lactamases* (Nova Science Publishers, New York, 2011).

[2] Pitout, J. D. & Laupland, K. B. Extended-spectrum beta-lactamase-producing Enterobacteriaceae: an emerging public-health concern. *Lancet Infect. Dis.* 8, 159-166 (2008).

[3] Edelstein, M. V. et. al. Spread of extensively resistant VIM-2-positive ST235 *Pseudomonas aeruginosa* in Belarus, Kazakhstan, and Russia: a longitudinal epidemiological and clinical study. *Lancet Infect. Dis.* 13, 867-876 (2013).

[4] Patel, G. & Bonomo, R. A. "Stormy waters ahead": global emergence of carbapenemases. *Frontiers Microbiol.* 4, 48 (2013).

[5] Frias, M. et al. New Delhi Metallo-β-Lactamase-Producing *Escherichia coli* Associated with Endoscopic Retrograde Cholangiopancreatography—Illinois, 2013. *MMWR* 62, 1051 (2014).

[6] Chang, Y. Laboratory Trends, December 17. 8 (BC Public Health Microbiology & Reference Laboratory, Vancouver, B C, 2013).

[7] Yigit, H. et al. Novel carbapenem-hydrolyzing beta-lactamase, KPC-1, from a carbapenem-resistant strain of *Klebsiella pneumoniae*. *Antimicrob. Agents nd Chemother.* 45, 1151-1161 (2001).

[8] Bush, K. Proliferation and significance of clinically relevant beta-lactamases. *Ann. NY Acad. Sci.* 1277, 84-90 (2013).

[9] Drawz, S. M. & Bonomo, R. A. Three decades of beta-lactamase inhibitors. *Clin. Microbiol. Rev.* 23, 160-201 (2010).
[10] Fast, W. & Sutton, L. D. Metallo-beta-lactamase: inhibitors and reporter substrates. *Biochim. Biophys. Acta* 1834, 1648-1659 (2013).
[11] Buynak, J. D. beta-Lactamase inhibitors: a review of the patent literature (2010-2013). *Expert Opin Ther Pat* 23, 1469-1481 (2013).
[12] Robert, M., Barbier, M., Lederer, E., Roux, L., Biemann, K., Vetter, W. Two new natural phytotoxins: aspergillomarasmine A and B and their relation to lycomarasmine and its derivatives. *Bulletin de la Societe Chimique de France* 187-188 (1962).
[13] Haenni, A. L. et al. Structure chimique des aspergillomarasmines A et B. *Helv. Chim. Acta* 48, 729-750 (1965).
[14] Mikami, Y. & Suzuki, T. Novel microbial inhibitors of angiotensin-converting enzyme, aspergillomarasmines A and B. *Agric. Biol. Chem.* 47, 2693-2695 (1983).
[15] Arai, K. et al. Aspergillomarasmine A and B, potent microbial inhibitors of endothelin-converting enzyme. *Biosci. Biotech. Biochem.* 57, 1944 (1993).
[16] Arai, Y., Nakakita, Y., Munakata, M., Ashizawa, N., Matsura, A. Aaspergillomarasmines as endothelin-converting enzyme inhibitors for treatment of hyperendothelinemia. JP 06192081, July (1994).
[17] Matsuura, A. et al. Pharmacological profiles of aspergillomarasmines as endothelin converting enzyme inhibitors. *Jap. J Ppharmacol.* 63, 187-193 (1993).
[18] Gaumann, E., Jaag, O., Baraun, R. Antibiotic-like action of plant viruses. *Experimentia* 3, 70-71 (1947).
[19] Ricci, D. P. & Silhavy, T. J. The Bam machine: a molecular cooper. *Biochim. Biophys. Acta* 1818, 1067-1084 (2012).
[20] Blair, J. M. & Piddock, L. J. Structure, function and inhibition of RND efflux pumps in Gram-negative bacteria: an update. *Curr. Op. Microbiol.* 12, 512-519 (2009).
[21] Holmquist, B., Bunning, P. & Riordan, J. F. A continuous spectrophotometric assay for angiotensin converting enzyme. *Anal Biochem* 95, 540-548 (1979)
[22] Zhang, J. H., Chung, T. D. & Oldenburg, K. R. A Simple Statistical Parameter for Use in Evaluation and Validation of High Throughput Screening Assays. *J. Biomol. Screen.* 4, 67-73 (1999).
[23] Haenni, A. L. et al. Structure chimique des aspergillomarasmines A et B. *Helv. Chimica Acta* 48, 729-750 (1965).
[24] Lee, M., Hesek, D. & Mobashery, S. A Practical Synthesis of Nitrocefin. *J. Org. Chem.* 70, 367-369 (2005).
[25] Matsuura, A. et al. Pharmacological profiles of aspergillomarasmines as endothelin converting enzyme inhibitors. *Jap. J. Ppharmacol.* 63, 187-193 (1993).
[26] King, D. T., Worrall, L. J., Gruninger, R. & Strynadka, N. C. New Delhi metallo-beta-lactamase: structural insights into beta-lactam recognition and inhibition. *J. Am. Chem. Soc.* 134, 11362-11365 (2012).
[27] Pillai, S. K., Moellering Jr, R. C. & Eliopoulos, G. M. in *Antibiotics in Laboratory Medicine* (ed V. Lorian) pp 365-440 (Williams & Wilkins, Philadelphia, 2005).
[28] EUCAST. Breakpoint tables for interpretation of MICs and zone diameters. Version 4.0, 2014. (2014).
[29] Hernandez Valladares, M. et al. Zn(II) dependence of the *Aeromonas hydrophila* AE036 metallo-beta-lactamase activity and stability. *Biochemistry* 36, 11534-11541 (1997).
[30] Shlaes, D. M. New beta-lactam-beta-lactamase inhibitor combinations in clinical development. *Ann. NY Acad. Sci.* 1277, 105-114 (2013).

The invention claimed is:
1. A pharmaceutical composition comprising:
one or more carbapenem antibiotic; and
an aspergillomarasmine A (AM-A) compound represented by:

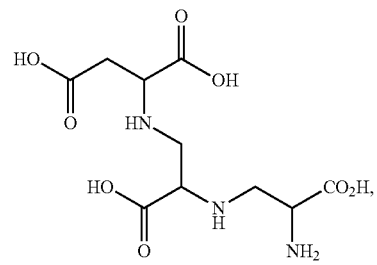 [SMILES: NC(CNC(CNC(CC(=O)O)C(=O)O)C(=O)O)C(=O)O]

or a pharmaceutically acceptable salt and/or solvate thereof; and
the one or more carbapenem antibiotic and the AM-A compound, or pharmaceutically acceptable salt and/or solvate thereof, are present in amounts that are effective to treat a bacterial infection, or a disease, disorder or condition arising from a bacterial infection,
wherein the bacterial infection is an infection of at least one metallo-β-lactamase (MBL)-expressing bacterium expressing bacterium.
2. The pharmaceutical composition of claim 1, wherein the AM-A compound or pharmaceutically acceptable salt and/or solvate thereof is a natural product extracted from a fungus.
3. The pharmaceutical composition of claim 2, wherein the fungus is *Aspergillus versicolor*.
4. The pharmaceutical composition of claim 2, wherein the AM-A compound, or pharmaceutically acceptable salt and/or solvate thereof, is obtainable by a process comprising a) evaporating *Aspergillus versicolor* under reduced pressure to provide a residue; b) purifying the residue using column chromatography to provide crude AM-A; and c) crystallizing the crude AM-A to provide purified AM-A.
5. The pharmaceutical composition of claim 1, wherein the MBL-expressing bacterium is at least one Verona integreon-encoded metallo-β-lactamase-expressing bacterium.
6. The pharmaceutical composition of claim 1, wherein the MBL-expressing bacterium is at least one New Delhi metallo-β-lactamase-expressing bacterium.
7. The pharmaceutical composition of claim 1, wherein the carbapenem antibiotic is selected from meropenem, biapenem, doripenem, ertapenem, panipenem and imipenem.
8. The pharmaceutical composition of claim 1, wherein the MBL-expressing bacterium is at least one carbapenem-resistant Gram-negative bacteria.
9. The pharmaceutical composition of claim 1, wherein the MBL-expressing bacterium is at least one bacterium belonging to the family Enterobacteriaceae, *Acinetobacter* or *Pseudomonas*.
10. A pharmaceutical composition comprising:
one or more β-lactam antibiotic; and
an aspergillomarasmine A (AM-A) compound represented by:

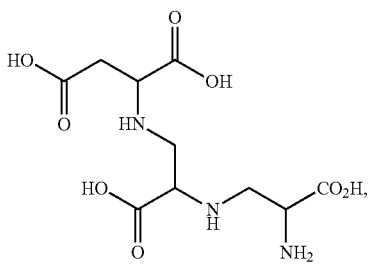

or a pharmaceutically acceptable salt and/or solvate thereof, and the one or more β-lactam antibiotic and the AM-A compound, or pharmaceutically acceptable salt and/or solvate thereof, are present in amounts that are effective for improving the efficacy of the one or more β-lactam antibiotic for the treatment of a bacterial infection or a disease, disorder or condition arising from a bacterial infection, wherein the one or more β-lactam antibiotic and the AM-A compound, or pharmaceutically acceptable salt and/or solvate thereof, are formulated in separate dosage forms, or the one or more β-lactam antibiotic and the AM-A compound or pharmaceutically acceptable salt and/or solvate thereof are formulated in a single dosage form, wherein the bacterial infection is an infection of at least one metallo-β-lactamase-expressing bacterium.

11. The pharmaceutical composition of claim 10, wherein the AM-A compound, or pharmaceutically acceptable salt and/or solvate thereof, is a natural product extracted from a fungus.

12. The pharmaceutical composition of claim 11, wherein the fungus is *Aspergillus versicolor*.

13. The pharmaceutical composition of claim 11, wherein the AM-A compound, or pharmaceutically acceptable salt and/or solvate thereof, is obtainable by a process comprising a) evaporating *Aspergillus versicolor* under reduced pressure to provide a residue; b) purifying the residue using column chromatography to provide crude AM-A; and c) crystallizing the crude AM-A to provide purified AM-A.

14. The pharmaceutical composition of claim 10, wherein the MBL-expressing bacterium is at least one Verona integreon-encoded metallo-β-lactamase-expressing bacterium or at least one New Delhi metallo-β-lactamase-expressing bacterium.

15. The pharmaceutical composition of claim 10, wherein the one or more β-lactam antibiotic is selected from penicillin derivatives, cephalosporins, monobactams and carbapenems.

16. The pharmaceutical composition of claim 10, wherein the one or more β-lactam antibiotic is a carbapenem antibiotic.

17. The pharmaceutical composition of claim 16, wherein the carbapenem antibiotic is selected from meropenem, biapenem, doripenem, ertapenem, panipenem and imipenem.

18. The pharmaceutical composition of claim 10, wherein the MBL-expressing bacterium is at least one carbapenem-resistant Gram-negative bacteria.

19. The pharmaceutical composition of claim 10, wherein the MBL-expressing bacterium is at least one bacterium belonging to the family Enterobacteriaceae, *Acinetobacter* or *Pseudomonas*.

20. The pharmaceutical composition of claim 10, wherein the β-lactam antibiotic and the AM-A compound, or pharmaceutically acceptable salt and/or solvate thereof, are formulated in a single dosage form.

21. The pharmaceutical composition of claim 10, wherein the β-lactam antibiotic and the AM-A compound, or pharmaceutically acceptable salt and/or solvate thereof, are formulated in separate dosage forms.

22. A method of treating a bacterial infection in a subject in need thereof comprising administering to the subject an effective amount of one or more β-lactam antibiotic in combination with an effective amount of an aspergillomarasmine A (AM-A) compound represented by:

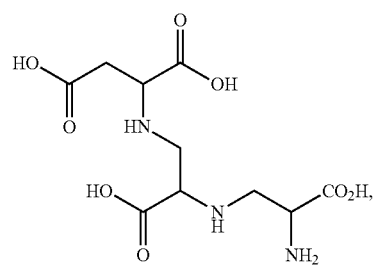 [SMILES: NC(CNC(CNC(CC(=O)O)C(=O)O)C(=O)O)C(=O)O]

or a pharmaceutically acceptable salt and/or solvate thereof, wherein the bacterial infection is an infection of at least one metallo-β-lactamase (MBL)-expressing bacterium.

23. The method of claim 22, wherein the MBL-expressing bacterium is at least one carbapenem-resistant Gram-negative bacteria.

24. The method of claim 22, wherein the MBL-expressing bacterium is at least one bacterium belonging to the family Enterobacteriaceae, *Acinetobacter* or *Pseudomonas*.

25. The method of claim 22, wherein the one or more β-lactam antibiotic is selected from penicillin derivatives, cephalosporins, monobactams and carbapenems.

26. The method of claim 25, wherein the one or more β-lactam antibiotic is the carbapenem antibiotic.

27. The method of claim 26, wherein the carbapenem antibiotic is selected from meropenem, biapenem, doripenem, ertapenem, panipenem and imipenem.

28. The method of claim 22, wherein the AM-A compound, or pharmaceutically acceptable salt and/or solvate thereof, is a natural product extracted from a fungus.

29. The method of claim 28, wherein the AM-A compound, or pharmaceutically acceptable salt and/or solvate thereof, is obtainable by a process comprising a) evaporating *Aspergillus versicolor* under reduced pressure to provide a residue; b) purifying the residue using column chromatography to provide crude AM-A; and c) crystallizing the crude AM-A to provide purified AM-A.

30. The method of claim 22, wherein the MBL-expressing bacterium is at least one Verona integreon-encoded metallo-β-lactamase-expressing bacterium or at least one New Delhi metallo-β-lactamase-expressing bacterium.

31. A method of improving the efficacy of a β-lactam antibiotic for treating a bacterial infection in a subject in need thereof comprising administering to the subject effective amount of a composition according to claim 10, wherein the bacterial infection is an infection of at least one metallo-β-lactamase (MBL)-expressing bacterium.

32. The method of claim 31, wherein the AM-A compound, or pharmaceutically acceptable salt and/or solvate thereof, is a natural product extracted from a fungus.

33. The method of claim 32, wherein the AM-A compound, or pharmaceutically acceptable salt and/or solvate thereof, is obtainable by a process comprising a) evaporating *Aspergillus versicolor* under reduced pressure to provide a residue; b) purifying the residue using column chromatography to provide crude AM-A; and c) crystallizing the crude AM-A to provide purified AM-A.

34. The method of claim 31, wherein the MBL-expressing bacterium is at least one one carbapenem-resistant Gram-negative bacteria.

35. The method of claim 31, wherein the MBL-expressing bacterium is at least one bacterium belonging to the family Enterobacteriaceae, *Acinetobacter* or *Pseudomonas*.

36. The method of claim 31, wherein the one or more β-lactam antibiotic is selected from penicillin derivatives, cephalosporins, monobactams and carbapenems.

37. The method of claim 31, wherein the one or more β-lactam antibiotic is a carbapenem antibiotic.

\* \* \* \* \*